(12) United States Patent
Burke et al.

(10) Patent No.: US 11,047,002 B2
(45) Date of Patent: Jun. 29, 2021

(54) SEQUENCING PROCESS

(71) Applicant: University of Technology, Sydney, Sydney (AU)

(72) Inventors: Catherine Maree Burke, Sydney (AU); Aaron Earl Darling, Sydney (AU)

(73) Assignee: Longas Technologies Pty Ltd, Sydney (AU)

( * ) Notice: Subject to any disclaimer, the term of this patent is extended or adjusted under 35 U.S.C. 154(b) by 527 days.

(21) Appl. No.: 15/313,705

(22) PCT Filed: May 22, 2015

(86) PCT No.: PCT/GB2015/051518
§ 371 (c)(1),
(2) Date: Nov. 23, 2016

(87) PCT Pub. No.: WO2015/177570
PCT Pub. Date: Nov. 26, 2015

(65) Prior Publication Data
US 2017/0183724 A1    Jun. 29, 2017

(30) Foreign Application Priority Data

May 23, 2014   (GB) .................................... 1409282

(51) Int. Cl.
*C12Q 1/6869*    (2018.01)
(52) U.S. Cl.
CPC .................. *C12Q 1/6869* (2013.01)
(58) Field of Classification Search
None
See application file for complete search history.

(56) References Cited

U.S. PATENT DOCUMENTS

2013/0237432 A1    9/2013   Li et al.

FOREIGN PATENT DOCUMENTS

WO    WO 2006/137734 A1    12/2006
WO    WO 2011/074960 A1    6/2011
(Continued)

OTHER PUBLICATIONS

Fabrice Armougom and Didier Raoult, Exploring Microbial Diversity Using 16S rRNA High-Throughput Methods JCSB/vol. 2 Jan.-Feb. 2009 (at www.omicsonline.com).*
(Continued)

*Primary Examiner* — Joseph Woitach
(74) *Attorney, Agent, or Firm* — Perkins Coie LLP

(57) ABSTRACT

The present invention relates to methods for generating sequences of template nucleic acid molecules, methods for determining sequences of at least two template nucleic acid molecules, computer programs adapted to perform the methods and computer readable media storing the computer programs. In particular the present invention relates to methods for generating sequences of at least one individual target template nucleic acid molecule comprising: a) providing at least one sample of nucleic acid molecules comprising at least two target template nucleic acid molecules; b) introducing a first molecular tag into one end of each of the at least two target template nucleic acid molecules and a second molecular tag into the other end of each of the at least two target template nucleic acid molecules to provide at least two tagged template nucleic acid molecules wherein each of the at least two tagged template nucleic acid molecules is tagged with a unique first molecular tag and a unique second molecular tag; c) amplifying the at least two tagged template nucleic acid molecules to provide multiple copies of the at least two tagged template nucleic acid molecules comprising the first molecular tag and the second (Continued)

molecular tag; d) sequencing regions of the at least two tagged template nucleic acid molecules comprising the first molecular tag and the second molecular tag; and e) reconstructing a consensus sequence for at least one of the at least two target template nucleic acid molecules.

17 Claims, 14 Drawing Sheets

Specification includes a Sequence Listing.

(56) References Cited

FOREIGN PATENT DOCUMENTS

| WO | WO 2012/061532 A1 | 5/2012 |
|---|---|---|
| WO | WO 2012/162267 A2 | 5/2012 |
| WO | 2012142213 A2 | 10/2012 |
| WO | WO 2013/130512 A2 | 9/2013 |
| WO | WO 2013/142389 A1 | 9/2013 |
| WO | WO 2013/163263 A2 | 10/2013 |
| WO | WO 2014/047556 A1 | 3/2014 |

OTHER PUBLICATIONS

Schloss et al (2011) Reducing the Effects of PCR Amplification and Sequencing Artifacts on 16S rRNA-Based Studies. PLoS ONE 6(12): e27310. doi:10.1371/journal.pone.0027310.*

Eggert et al. Multiplex-PCR-Based Recombination as a Novel High-Fidelity Method for Directed Evolution ChemBioChem 2005, 6, 1062-1067 DOI: 10.1002/cbic.200400417.*

Burke et al., "Resolving microbial microdiversity with high accuracy, full length 16S rRNA Illumina sequencing," bioRxiv, doi: 10.1101/010967 (10 pages) (Nov. 2014).

Kozich et al., "Development of a Dual-Index Sequencing Strategy and Curation Pipeline for Analyzing Amplicon Sequence Data on the MiSeq Illumina Sequencing Platform," Applied and Environmental MicroBiology, 79 (17):5112-5120 (Sep. 2013).

Opposition Against European Patent No. EP 3 146 070, submitted in EP 3 146 070 and first reported to applicant by the EPO on Jul. 8, 2019 (25 pages).

Illumina "An introduction to Next Generation Sequencing Technology," Illumina website, available on the worldwide web at web.archive.org/web/20130517224900/https://www.illumina.com/documents/products/illumina_seauencing_introduction.pdf (published online on May 17, 2013).

Islam et al., "Quantitative single-cell RNA-seq with unique molecular identifiers," Nature Methods, vol. 11, pp. 163-166 (Feb. 2014; published online Dec. 22, 2013).

Kinde et al., "Detection and quantification of rare mutations with massively parallel sequencing," PNAS, vol. 108, No. 23, pp. 9530-9535 (Jun. 7, 2011).

Schmitt et al., "Detection of ultra-rare mutations by next-generation sequencing," PNAS, vol. 109, No. 36, pp. 14508-14513 (Sep. 4, 2012).

Communication pursuant to Article 94(3) EPC, European Application No. 15 727 042.2 (published as EP 3 146 070) (8 pages) (dated Jan. 31, 2018).

Reply to examination report, European Application No. 15 727 042.2 (published as EP 3 146 070) (38 pages) (dated Apr. 30, 2018).

Intention to grant under Rule 71(3) EPC, European Application No. 15 727 042.2 (published as EP 3 146 070) (124 pages) (dated May 28, 2018).

Hiatt et al., "Single molecule molecular inversion probes for targeted, high-accuracy detection of low-frequency variation," Genome Research, 23:843-854 (Feb. 2013).

Jabara et aL., Accurate sampling and deep sequencing of the HIV-1 protease gene using a Primer ID, PNAS, 108(50):20166-20171 (Dec. 13, 2011).

Vollmers et al., "Genetic measurement of memory B-cell recall using antibody repertoire sequencing," PNAS, 110(33)1 3463-13468 (Aug. 13, 2013).

Burke et al., "Resolving microbial microdiversity with high accuracy, full length 16S rRNA Illumina sequencing," bioRxiv, doi: 10.1101/010967 (10 pages) (Nov. 2014).

Caporaso et al., "QIIME allows analysis of high-throughput community sequencing data," Nat. Methods, 7(5):335-336 (May 2010).

Caporaso et al., "Ultra-high-throughput microbial community analysis on the Illumina HiSeq and MiSeq platforms," *The ISME Journal*, 6:1621-1624 (2012).

Clarke et al., "Modular tagging of amplicons using a single PCR for high-throughput sequencing," *Molecular Ecology Resources*, 14:117-121 (2014).

Cole et al., "Highly Accurate Sequencing of Full-Length Immune Repertoire Amplicons Using Tn5-Enabled and Molecular Identifier-Guided Amplicon Assembly," *J. Immunol.*, 196:2902-2907 (prepublished online Feb. 8, 2016).

Darlling et al., "The genome of Clostridium difficile 5.3," *Gut Pathogens*, 6:4 (2014).

Edgar, "Search and clustering orders of magnitude faster than BLAST," *Bioinformatics*, 26(19):2460-2461 (2010).

Edgar, "UPARSE: highly accurate OUT sequences from microbial amplicon reads," *Nat. Methods*, 10(10):996-998 (Oct. 2013).

Karst et al. "Thousands of primer-free, high-quality, full-length Ssu rRNA sequences from all domains of life," *bioRxiv 070771*, doi: (2016).10.1101/070771 (10 pages).

Lundberg et al., "Practical innovations for high-throughput amplicon sequencing," *Nat. Methods*, 10(10):999-1002 (Oct. 2013).

Schloss, "The Effects of Alignment Quality, Distance Calculation Method, Sequence Filtering, and Region on the Analysis of 16S rRNA Gene-Based Studies," *PloS Computyational Biology*, 6(7):1-16 (Jul. 2010).

Tritt et al., "An Integrated Pipeline for de Novo Assembly of Microbial Genomes," *PloS One*, 7(9):e42304 (9 pages) (Sep. 13, 2012).

Turner et al., "Investigating Deep Phylogenetic Relationships among Cyanobacteria and Plastids by Small Subunit rRNA Sequence Analysis," *J. Eukaryot. Microbiol.*, 46(4):327-338 (1999).

Weisburg et al., "16S Ribosomal DNA Amplification for Phylogenetic Study," *Journal of Bacteriology*, pp. 697-703 (Jan. 1991).

* cited by examiner

Figure 2a

Table 1: Primers used for 16S gene amplification and sequencing

| Primer name | Sequence |
| --- | --- |
| Long_forward_1 | ACACTCTTTCCCTACACGACGCTCTTCCGATCTNNNNNNNNNNGTTGGCCGCGAGAGTTTGATCMTGGCTCAG |
| Long_forward_2 | ACACTCTTTCCCTACACGACGCTCTTCCGATCTNNNNNNNNNNTATTAACTNCGAGAGTTTGATCMTGGCTCAG |
| Long_forward_3 | ACACTCTTTCCCTACACGACGCTCTTCCGATCTNNNNNNNNNNCTAATGGCNNCGAGAGTTTGATCMTGGCTCAG |
| Long_forward_4 | ACACTCTTTCCCTACACGACGCTCTTCCGATCTNNNNNNNNNNAACCAGTCNNCGAGAGTTTGATCMTGGCTCAG |
| Long_forward_5 | ACACTCTTTCCCTACACGACGCTCTTCCGATCTNNNNNNNNNNGAACGGAGCGAGAGTTTGATCMTGGCTCAG |
| Long_forward_6 | ACACTCTTTCCCTACACGACGCTCTTCCGATCTNNNNNNNNNNACTGAAGTNCGAGAGTTTGATCMTGGCTCAG |
| Long_forward_7 | ACACTCTTTCCCTACACGACGCTCTTCCGATCTNNNNNNNNNNTTGGCTATNNCGAGAGTTTGATCMTGGCTCAG |
| Long_forward_8 | ACACTCTTTCCCTACACGACGCTCTTCCGATCTNNNNNNNNNNTGGCGATTNNCGAGAGTTTGATCMTGGCTCAG |
| Long_forward_9 | ACACTCTTTCCCTACACGACGCTCTTCCGATCTNNNNNNNNNNCCTCTGATCGAGAGTTTGATCMTGGCTCAG |
| Long_forward_10 | ACACTCTTTCCCTACACGACGCTCTTCCGATCTNNNNNNNNNNCTCATGCGNCGAGAGTTTGATCMTGGCTCAG |
| Long_forward_11 | ACACTCTTTCCCTACACGACGCTCTTCCGATCTNNNNNNNNNNTTCAGCGANNCGAGAGTTTGATCMTGGCTCAG |
| Long_forward_12 | ACACTCTTTCCCTACACGACGCTCTTCCGATCTNNNNNNNNNNGGATGCCANNNCGAGAGTTTGATCMTGGCTCAG |
| Long_forward_13 | ACACTCTTTCCCTACACGACGCTCTTCCGATCTNNNNNNNNNNCGGTCGAGCGAGAGTTTGATCMTGGCTCAG |
| Long_forward_14 | ACACTCTTTCCCTACACGACGCTCTTCCGATCTNNNNNNNNNNAAGACTACNCGAGAGTTTGATCMTGGCTCAG |
| Long_forward_15 | ACACTCTTTCCCTACACGACGCTCTTCCGATCTNNNNNNNNNNAACGCTAANNCGAGAGTTTGATCMTGGCTCAG |
| Long_forward_16 | ACACTCTTTCCCTACACGACGCTCTTCCGATCTNNNNNNNNNNGCCTACGCNNNCGAGAGTTTGATCMTGGCTCAG |
| Long_forward_17 | ACACTCTTTCCCTACACGACGCTCTTCCGATCTNNNNNNNNNNTGACTGCTCGAGAGTTTGATCMTGGCTCAG |
| Long_forward_19 | ACACTCTTTCCCTACACGACGCTCTTCCGATCTNNNNNNNNNNCAACCTTANNCGAGAGTTTGATCMTGGCTCAG |
| Long_forward_20 | ACACTCTTTCCCTACACGACGCTCTTCCGATCTNNNNNNNNNNGGAGGCTGNNNCGAGAGTTTGATCMTGGCTCAG |
| Long_forward_21 | ACACTCTTTCCCTACACGACGCTCTTCCGATCTNNNNNNNNNNAATCGATACGAGAGTTTGATCMTGGCTCAG |
| Long_forward_22 | ACACTCTTTCCCTACACGACGCTCTTCCGATCTNNNNNNNNNNACCAATTGNCGAGAGTTTGATCMTGGCTCAG |

Figure 2b

| Long_forward_23 | ACACTCTTTCCCTACACGACGCTCTTCCGATCTNNNNNNNNNNCCTAATAANNCGAGAGTTTGATCMTGGCTCAG |
| --- | --- |
| Long_forward_24 | ACACTCTTTCCCTACACGACGCTCTTCCGATCTNNNNNNNNNNGGATTAGGNNNCGAGAGTTTGATCMTGGCTCAG |
| Long_forward_25 | ACACTCTTTCCCTACACGACGCTCTTCCGATCTNNNNNNNNNNGCGTTACCCGAGAGTTTGATCMTGGCTCAG |
| Long_reverse_1 | CTCGGCATTCCTGCTGAACCGCTCTTCCGATCTNNNNNNNNNNGTTGGCCGTAGACGGGCGGTGTGTRCA |
| Long_reverse_2 | CTCGGCATTCCTGCTGAACCGCTCTTCCGATCTNNNNNNNNNNTATTAACTNNNTAGACGGGCGGTGTGTRCA |
| Long_reverse_3 | CTCGGCATTCCTGCTGAACCGCTCTTCCGATCTNNNNNNNNNNCTAATGGCTAGACGGGCGGTGTGTRCA |
| Long_reverse_4 | CTCGGCATTCCTGCTGAACCGCTCTTCCGATCTNNNNNNNNNNAACCAGTCNNNTAGACGGGCGGTGTGTRCA |
| Long_reverse_5 | CTCGGCATTCCTGCTGAACCGCTCTTCCGATCTNNNNNNNNNNGAACGGAGTAGACGGGCGGTGTGTRCA |
| Long_reverse_6 | CTCGGCATTCCTGCTGAACCGCTCTTCCGATCTNNNNNNNNNNACTGAAGTNNTAGACGGGCGGTGTGTRCA |
| Long_reverse_7 | CTCGGCATTCCTGCTGAACCGCTCTTCCGATCTNNNNNNNNNNTTGGCTATNNNTAGACGGGCGGTGTGTRCA |
| Long_reverse_8 | CTCGGCATTCCTGCTGAACCGCTCTTCCGATCTNNNNNNNNNNTGGCGATTTAGACGGGCGGTGTGTRCA |
| Long_reverse_9 | CTCGGCATTCCTGCTGAACCGCTCTTCCGATCTNNNNNNNNNNCCTCTGATNTAGACGGGCGGTGTGTRCA |
| Long_reverse_10 | CTCGGCATTCCTGCTGAACCGCTCTTCCGATCTNNNNNNNNNNCTCATGCGNNTAGACGGGCGGTGTGTRCA |
| Long_reverse_11 | CTCGGCATTCCTGCTGAACCGCTCTTCCGATCTNNNNNNNNNNTTCAGCGANTAGACGGGCGGTGTGTRCA |
| Long_reverse_12 | CTCGGCATTCCTGCTGAACCGCTCTTCCGATCTNNNNNNNNNNGGATGCCANNTAGACGGGCGGTGTGTRCA |
| Long_reverse_13 | CTCGGCATTCCTGCTGAACCGCTCTTCCGATCTNNNNNNNNNNCGGTCGAGNTAGACGGGCGGTGTGTRCA |
| Long_reverse_14 | CTCGGCATTCCTGCTGAACCGCTCTTCCGATCTNNNNNNNNNNAAGACTACNNNTAGACGGGCGGTGTGTRCA |
| Long_reverse_15 | CTCGGCATTCCTGCTGAACCGCTCTTCCGATCTNNNNNNNNNNAACGCTAATAGACGGGCGGTGTGTRCA |
| Long_reverse_16 | CTCGGCATTCCTGCTGAACCGCTCTTCCGATCTNNNNNNNNNNGCCTACGCNTAGACGGGCGGTGTGTRCA |
| Long_reverse_17 | CTCGGCATTCCTGCTGAACCGCTCTTCCGATCTNNNNNNNNNNTGACTGCTNNTAGACGGGCGGTGTGTRCA |
| Long_reverse_18 | CTCGGCATTCCTGCTGAACCGCTCTTCCGATCTNNNNNNNNNNATTGCCGCNTAGACGGGCGGTGTGTRCA |
| Long_reverse_19 | CTCGGCATTCCTGCTGAACCGCTCTTCCGATCTNNNNNNNNNNCAACCTTANNTAGACGGGCGGTGTGTRCA |

Figure 2c

| Long_reverse_20 | CTCGGCATTCCTGCTGAACCGCTCTTCCGATCTNNNNNNNNNNGGAGGCTGNTAGACGGGCGGTGTGTRCA |
| --- | --- |
| Long_reverse_21 | CTCGGCATTCCTGCTGAACCGCTCTTCCGATCTNNNNNNNNNNAATCGATANNTAGACGGGCGGTGTGTRCA |
| Long_reverse_22 | CTCGGCATTCCTGCTGAACCGCTCTTCCGATCTNNNNNNNNNNACCAATTGNTAGACGGGCGGTGTGTRCA |
| Long_reverse_23 | CTCGGCATTCCTGCTGAACCGCTCTTCCGATCTNNNNNNNNNNCCTAATAANTAGACGGGCGGTGTGTRCA |
| Long_reverse_24 | CTCGGCATTCCTGCTGAACCGCTCTTCCGATCTNNNNNNNNNNGGATTAGGNNTAGACGGGCGGTGTGTRCA |
| Long_reverse_25 | CTCGGCATTCCTGCTGAACCGCTCTTCCGATCTNNNNNNNNNNGCGTTACCNNNTAGACGGGCGGTGTGTRCA |
| PE_1 | AATGATACGGCGACCACCGAGATCTACACTCTTTCCCTACACGACG |
| PE_2 | CAAGCAGAAGACGGCATACGAGATCGGTCTCGGCATTCCTGCTGAACCG |
| Caporaso_forward_1 | AATGATACGGCGACCACCGAGATCTACACAACCAGTCTATGGTAATTGTGTGCCAGCMGCCGCGGTAA |
| Caporaso_forward_2 | AATGATACGGCGACCACCGAGATCTACACAACGCTAATATGGTAATTGTGTGCCAGCMGCCGCGGTAA |
| Caporaso_forward_3 | AATGATACGGCGACCACCGAGATCTACACAAGACTACTATGGTAATTGTGTGCCAGCMGCCGCGGTAA |
| Caporaso_forward_4 | AATGATACGGCGACCACCGAGATCTACACAATCGATATATGGTAATTGTGTGCCAGCMGCCGCGGTAA |
| Caporaso_forward_5 | AATGATACGGCGACCACCGAGATCTACACACCAATTGTATGGTAATTGTGTGCCAGCMGCCGCGGTAA |
| Caporaso_forward_6 | AATGATACGGCGACCACCGAGATCTACACACTGAAGTTATGGTAATTGTGTGCCAGCMGCCGCGGTAA |
| Caporaso_forward_7 | AATGATACGGCGACCACCGAGATCTACACATTGCCGCTATGGTAATTGTGTGCCAGCMGCCGCGGTAA |
| Caporaso_forward_8 | AATGATACGGCGACCACCGAGATCTACACCAACCTTATGGTAATTGTGTGCCAGCMGCCGCGGTAA |
| Caporaso_forward_9 | AATGATACGGCGACCACCGAGATCTACACCCTAATAATATGGTAATTGTGTGCCAGCMGCCGCGGTAA |
| Caporaso_forward_10 | AATGATACGGCGACCACCGAGATCTACACCCTCTGATTATGGTAATTGTGTGCCAGCMGCCGCGGTAA |
| Caporaso_forward_14 | AATGATACGGCGACCACCGAGATCTACACGAACGGAGTATGGTAATTGTGTGCCAGCMGCCGCGGTAA |
| Caporaso_forward_16 | AATGATACGGCGACCACCGAGATCTACACGCGTTACCTATGGTAATTGTGTGCCAGCMGCCGCGGTAA |
| Caporaso_forward_18 | AATGATACGGCGACCACCGAGATCTACACGGATGCCATATGGTAATTGTGTGCCAGCMGCCGCGGTAA |
| Caporaso_forward_20 | AATGATACGGCGACCACCGAGATCTACACGTTGGCCGTATGGTAATTGTGTGCCAGCMGCCGCGGTAA |
| Caporaso_forward_22 | AATGATACGGCGACCACCGAGATCTACACTGACTGCTTATGGTAATTGTGTGCCAGCMGCCGCGGTAA |

Figure 2d

| Caporaso_forward_24 | AATGATACGGCGACCACCGAGATCTACACTTCAGCGATATGGTAATTGTGTGCCAGCMGCCGCGGTAA |
|---|---|
| Caporaso_reverse_1 | CAAGCAGAAGACGGCATACGAGATAACCAGTCAGTCAGTCAGCCGGACTACHVGGGTWTCTAAT |
| Caporaso_reverse_7 | CAAGCAGAAGACGGCATACGAGATATTGCCGCAGTCAGTCAGCCGGACTACHVGGGTWTCTAAT |
| Caporaso_reverse_8 | CAAGCAGAAGACGGCATACGAGATCAACCTTAAGTCAGTCAGCCGGACTACHVGGGTWTCTAAT |
| Caporaso_reverse_9 | CAAGCAGAAGACGGCATACGAGATCCTAATAAAGTCAGTCAGCCGGACTACHVGGGTWTCTAAT |
| Caporaso_reverse_15 | CAAGCAGAAGACGGCATACGAGATGCCTACGCAGTCAGTCAGCCGGACTACHVGGGTWTCTAAT |
| Caporaso_reverse_16 | CAAGCAGAAGACGGCATACGAGATGCGTTACCAGTCAGTCAGCCGGACTACHVGGGTWTCTAAT |
| Caporaso_reverse_17 | CAAGCAGAAGACGGCATACGAGATGGAGGCTGAGTCAGTCAGCCGGACTACHVGGGTWTCTAAT |
| Caporaso_reverse_23 | CAAGCAGAAGACGGCATACGAGATTGGCGATTAGTCAGTCAGCCGGACTACHVGGGTWTCTAAT |
| Caporaso_reverse_24 | CAAGCAGAAGACGGCATACGAGATTTCAGCGAAGTCAGTCAGCCGGACTACHVGGGTWTCTAAT |
| Caporaso_reverse_25 | CAAGCAGAAGACGGCATACGAGATTTGGCTATAGTCAGTCAGCCGGACTACHVGGGTWTCTAAT |
| Illumina_E_1 | AATGATACGGCGACCACCGA |
| Illumina_E_2 | CAAGCAGAAGACGGCATACGA |
| Caporaso_read_1 | TATGGTAATTGTGTGCCAGCMGCCGCGGTAA |
| Caporaso_read_2 | AGTCAGTCAGCCGGACTACHVGGGTWTCTAAT |
| Caporaso_index_read | ATTAGAWACCCBDGTAGTCCGGCTGACTGACT |

SEQUENCING PROCESS

CROSS-REFERENCE TO RELATED APPLICATIONS

This application is a 35 U.S.C. § 371 application of International Application No. PCT/GB2015/051518, filed May 22, 2015, which claims the benefit of British Patent Application No. 1409282.9, filed May 23, 2014, each of which applications is incorporated herein by reference in its entirety.

INCORPORATION OF SEQUENCE LISTING

This application contains a sequence listing submitted electronically via EFS-web, which serves as both the paper copy and the computer readable form (CRF) and consists of a file entitled "123851-8001US00 seq_list.txt", which was created on Nov. 21, 2016, which is 28,672 bytes in size, and which is herein incorporated by reference in its entirety.

TECHNICAL FIELD

The present invention relates to methods for generating sequences of template nucleic acid molecules, methods for determining sequences of at least two template nucleic acid molecules, computer programs adapted to perform the methods and computer readable media storing the computer programs.

BACKGROUND

In general there are difficulties with sequencing long nucleic acid sequences (for example those greater than 1 Kbp) effectively and quickly. Presently sequencing technology can produce either large volumes of short sequence reads (i.e. sequences of short nucleic acid molecules) or small numbers of long sequence reads. It is, at present, difficult to sequence large numbers of long sequence reads.

The 16S rRNA gene is used for phylogenetic studies as it is highly conserved between different species of bacteria and archaea. In addition to highly conserved primer binding sites, 16S rRNA gene sequences contain hypervariable regions that can provide species-specific signature sequences useful for bacterial identification. As a result, 16S rRNA gene sequencing has become prevalent in medical microbiology as a rapid and cheap alternative to phenotypic methods of bacterial identification. In addition, although it was originally used to identify bacteria, 16S sequencing was subsequently found to be capable of reclassifying bacteria into completely new species, or even genera. It has also become one of the primary criteria used to identify and describe new species of bacteria, both in laboratory culture and in uncultured environmental samples. However, the use of 16S rRNA sequence analysis is hampered due to the difficulties associated with sequencing large numbers of nucleic acid molecules greater than 1 Kbp. This has meant that, in general, most researchers performing 16S sequence analysis tend to focus on short, up to 500 bp, regions of the 16S gene. Sequencing such short regions results in a lack of taxonomic resolution.

In addition general sequencing methods tend to lack accuracy due to recombination events that can occur during the sequencing process. Sequencing involves steps of amplifying the nucleic acid molecules to be sequenced. During these amplification steps recombination events can occur. This can mean that when samples of nucleic acid molecules contain genes of similar sequences, sequencing methods will generate, not only the sequences of the original genes, but also the sequences of nucleic acid molecules produced via recombination between these similar genes. Since 16S rRNA genes tend to be similar across different species, a nucleic acid template molecule within a sample of nucleic acid molecules comprising nucleic acid molecules from multiple different 16S rRNA genes may recombine during sequencing. Such recombination events become increasingly frequent as the amount of amplification required to analyse the sample grows, especially at levels required to analyse certain host-associated microbiota and forensic samples. Thus it is beneficial, when sequencing samples of DNA having 16S rRNA genes, to be able to identify and remove sequences of nucleic acids produced via recombination.

Computational methods for detecting recombination are limited, however, because they can only detect recombination events that occur between two parental molecules that are substantially different in sequence. Recombination among highly similar sequences (e.g. >97% identity) remains difficult to discriminate from true biological diversity using computational methods. Molecular approaches to boost the accuracy of computational recombination detection do not currently exist.

Approaches to boost the read length of high-throughput sequencing instruments have been described previously. Among these are the complexity reduction approaches such as Illumina's Moleculo which assigns unique barcodes to pools of 100 s of DNA molecules, and molecular tagging methods, which add a unique barcode to each single molecule in a sample. Both approaches reconstruct the original template molecules by analysing a collection of short reads belonging to each barcode, computationally reconstructing a consensus sequence of the original templates. Both approaches depend on amplification to create many copies of the barcoded pools or tagged single molecules. However, none of these previous approaches employ a molecular system to detect in-vitro recombination error introduced by the amplification.

SUMMARY OF THE INVENTION

The present inventors have developed a technique which allows for sequencing of long sequences of nucleic acids quickly and accurately. This technique can be used in many different applications but is particularly advantageous for use in 16S rRNA gene sequencing since it can be used to generate large volumes of long reads spanning the entire length of the 1.5 Kbp gene. Thus this technique can be used to sequence the entire 16S rRNA gene providing greater taxonomic resolution than previous methods which involved sequencing shorter regions of the 16S rRNA gene.

In addition the present inventors have developed a technique which allows for sequences of recombination products generated during the sequencing process to be identified and disregarded. This improves the sensitivity and accuracy of sequencing in general and such accuracy improves the taxonomic resolution when the technique is used for phylogenetic studies using 16S sequencing.

In a first aspect of the present invention there is provided a method for generating sequences of at least one individual template nucleic acid molecule which is greater than 1 Kbp in size comprising:

a) providing at least one sample of nucleic acid molecules comprising at least two template nucleic acid molecules which are greater than 1 Kbp in size;

b) introducing a first molecular tag into one end of each of the at least two target template nucleic acid molecules and a second molecular tag into the other end of each of the at least two target template nucleic acid molecules to provide at least two tagged template nucleic acid molecules wherein each of the at least two tagged template nucleic acid molecules is tagged with a unique first molecular tag and a unique second molecular tag;

c) amplifying the at least two tagged template nucleic acid molecules to provide multiple copies of the at least two tagged template nucleic acid molecules;

d) isolating a fraction of the multiple copies of the at least two tagged template nucleic acid molecules and fragmenting the tagged template nucleic acid molecules in the fraction to provide multiple fragmented template nucleic acid molecules;

e) sequencing regions of the multiple copies of the at least two tagged template nucleic acid molecules comprising the first molecular tag and the second molecular tag;

f) sequencing the multiple fragmented template nucleic acid molecules; and g) reconstructing a consensus sequence for at least one of the at least two template nucleic acid molecules from sequences comprising at least a subset of the sequences produced in step f).

In a second aspect of the present invention there is provided a method for determining sequences of at least one individual target template nucleic acid molecule comprising the following steps:

(a) obtaining data comprising sequences of regions of multiple copies of at least two tagged template nucleic acid molecules wherein each of the at least two tagged template nucleic acid molecules comprises a first molecular tag at one end and a second molecular tag at the other end, wherein each target template nucleic acid molecule is tagged with a unique first molecular tag and a unique second molecular tag and wherein the regions comprise the first molecular tag and the second molecular tag;

(b) analysing the data comprising sequences of regions of the at least two tagged template nucleic acid molecules comprising the first molecular tag and the second molecular tag to identify clusters of sequences which are likely to correspond to the same individual target template nucleic acid molecule by assigning sequences comprising first molecular tags which are homologous to one another and second molecular tags which are homologous to one another to the same cluster;

(c) obtaining data comprising sequences of multiple fragments of the at least two tagged template nucleic acid molecules wherein each of the fragments comprise either the first molecular tag or the second molecular tag;

(d) analysing the sequences of the multiple fragments of the at least two tagged template nucleic acid molecules to identify sequences of the multiple fragments of the at least two tagged template nucleic acid molecules which comprise the first molecular tag which is homologous to the first molecular tag of the sequences of a first cluster or the second molecular tag which is homologous to the second molecular tag of the sequences of the first cluster;

(e) reconstructing the sequence of a first target template nucleic acid molecule by aligning sequences comprising at least a subset of the sequences of the multiple fragments of the at least two tagged template nucleic acid molecules identified in step (d) and defining a consensus sequence from these sequences; and (f) performing steps (c) to (e) in respect of a second and/or further template nucleic acid molecule.

In a third aspect of the invention there is provided a method for determining sequences of at least one target template nucleic acid molecule comprising the following steps:

(a) obtaining data comprising clusters of sequences wherein:

(i) each cluster comprises sequences of regions of multiple copies of at least two tagged template nucleic acid molecules wherein each of the at least two tagged template nucleic acid molecules comprises a first molecular tag at one end and a second molecular tag at the other end, wherein each of the at least two target template nucleic acids is tagged with a unique first molecular tag and a unique second molecular tag and wherein the regions comprise the first molecular tag and the second molecular tag;

(ii) each cluster comprises sequences of multiple fragments of the at least two tagged template nucleic acid molecules wherein each of the fragments comprises either the first molecular tag or the second molecular tag;

(iii) the sequences of regions of multiple copies of at least two tagged template nucleic acid molecules in each cluster comprise first molecular tags and second molecular tags which are homologous to one another;

(iv) the sequences of the multiple fragments of the at least two tagged template nucleic acid molecules comprise the first molecular tag which is homologous to the first molecular tag of the sequences of regions of the multiple copies of at least two target template nucleic acid molecules in that cluster or the second molecular tag which is homologous to the second molecular tag of the sequences of regions of multiple copies of the at least two tagged template nucleic acid molecules in that cluster;

(b) reconstructing the sequence of a first template nucleic acid molecule by aligning sequences comprising at least a subset of the sequences of the multiple fragments of the at least two tagged template nucleic acid molecules in a first cluster and defining a consensus sequence from these sequences; and (c) performing step (b) in respect of a second and/or further template nucleic acid molecule.

In a fourth aspect of the invention there is provided a method generating sequences of at least one individual target template nucleic acid molecule comprising:

a) providing at least one sample of nucleic acid molecules comprising at least two template nucleic acid molecules;

b) introducing a first molecular tag into one end of each of the at least two target template nucleic acid molecules and a second molecular tag into the other end of each of the at least two target template nucleic acid molecules to provide at least two tagged template nucleic acid molecules wherein each of the at least two tagged template nucleic acid molecules is tagged with a unique first molecular tag and a unique second molecular tag;

c) amplifying the at least two tagged template nucleic acid molecules provide multiple copies of the at least two tagged template nucleic acid molecules;

d) sequencing regions of the at least two tagged template nucleic acid molecules comprising the first molecular tag and the second molecular tag; and e) reconstructing a consensus sequence for at least one of the at least two target template nucleic acid molecules wherein step e) comprises (i) identifying clusters of sequences of the regions of the multiple copies of the at least two tagged template nucleic acid molecules which are likely to correspond to the same target template nucleic acid molecule by assigning sequences comprising first molecular tag sequences which are homologous to one another and second molecular tag sequences which are homologous to one another to the same cluster;

(ii) selecting at least one cluster of sequences wherein the sequences within the selected clusters comprise a first molecular tag and a second molecular tag which are more commonly associated with one another than with a different first molecular tag or second molecular tag;

(iii) reconstructing a consensus sequence of a first target template nucleic acid molecule by aligning sequences of the at least two template nucleic acid molecules in the cluster selected in step (ii) and defining a consensus sequence from these sequences; and (iv) performing steps (ii) to (iii) in respect of a second and/or further template nucleic acid molecule.

In a fifth aspect of the invention there is provided a method for determining sequences of at least one individual target template nucleic acid molecule comprising the following steps:

(a) obtaining data comprising sequences of regions of multiple copies of at least two tagged template nucleic acid molecules wherein each of the at least two tagged template nucleic acid molecules comprises a first molecular tag at one end and a second molecular tag at the other end, wherein each target template nucleic acid molecule is tagged with a unique first molecular tag and a unique second molecular tag and wherein the regions comprise the first molecular tag and the second molecular tag;

(b) analysing the data comprising sequences of regions of the at least two tagged template nucleic acid molecules comprising the first molecular tag and the second molecular tag to identify clusters of sequences which are likely to correspond to the same template nucleic acid molecule by assigning sequences comprising first molecular tags which are homologous to one another and second molecular tags which are homologous to one another to the same cluster;

(c) selecting at least one cluster of sequences wherein the sequences within the selected clusters comprise a first molecular tag and a second molecular tag which are more commonly associated with one another than with a different first molecular tag or second molecular tag;

(d) reconstructing a consensus sequence of a first template nucleic acid molecule by aligning at least a subset of the sequences molecules in the cluster selected in step (c) and defining a consensus sequence from these sequences; and (e) performing steps (c) to (d) in respect of a second and/or further template nucleic acid molecule.

In a sixth aspect of the invention there is provided a method for determining sequences of at least one target template nucleic acid molecule comprising (a) obtaining data comprising a cluster of sequences;

(b) reconstructing a consensus sequence of a first template nucleic acid molecule by aligning the sequences of at least a subset of the sequences in the selected cluster;

wherein the sequences in the selected cluster comprise sequences of regions of multiple copies of at least two tagged template nucleic acid molecules wherein each of the at least two tagged template nucleic acid molecules comprises a first molecular tag at one end and a second molecular tag at the other end, wherein each target template nucleic acid molecule is tagged with a unique first molecular tag and a unique second molecular tag and wherein the regions comprise the first molecular tag and the second molecular tag; and each sequence in the selected cluster (i) comprises first molecular tag which is homologous to the first molecular tag of the other sequences in that and the second molecular tag which is homologous to the second molecular tag of the other sequences in that cluster;

(ii) comprises a first molecular tag and a second molecular tag which are more commonly associated with one another than with a different first molecular tag or second molecular tag.

In a seventh aspect of the invention there is provided a computer program adapted to perform the methods or method steps of the invention when said program is run on an electronic device.

In an eighth aspect of the invention there is provided a computer readable medium storing the computer program of the invention.

In a ninth aspect of the invention there is provided a kit comprising:

(i) primers comprising a portion comprising a first molecular tag or a second molecular tag and a portion having a sequence that is capable of hybridising to at least two template nucleic acid molecules;

(ii) instructions describing how to perform the method of the invention.

In a tenth aspect of the invention there is provided a kit comprising (i) primers comprising a portion comprising a first molecular tag or a second molecular tag and a portion having a sequence that is capable of hybridising to at least two template nucleic acid molecules;

(ii) the computer readable medium storing the computer program of the invention.

DESCRIPTION OF FIGURES

FIG. 2. Description of sequences of primers used for 16S gene amplification and sequencing.

DETAILED DESCRIPTION OF THE INVENTION

Figure 1:
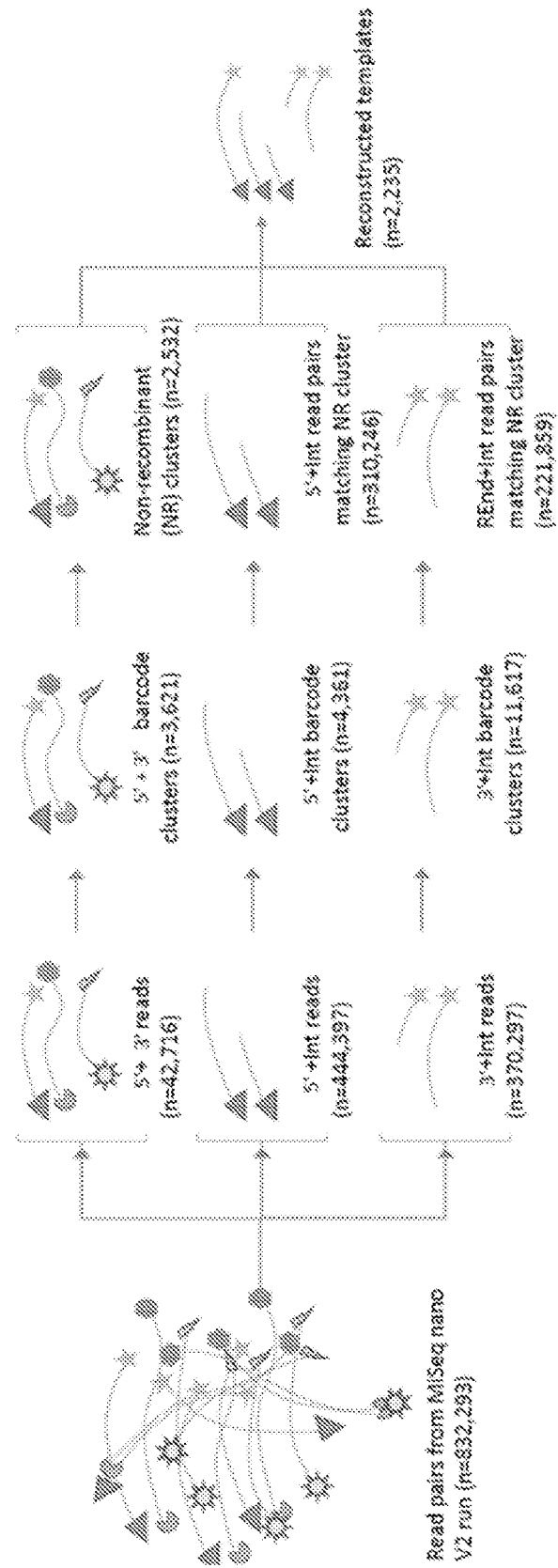
FIG. 1. Fully automated computational workflow used for processing reads from a single MiSeq nano run to sequence full length 16S rRNA templates. A pool of molecules containing both full length templates and "fill-in" fragments was sequenced on the instrument and processed computationally using the steps shown.

Generating or Determining Sequences of at Least One Individual Target Template Nucleic Acid Molecule The present method provides a method for generating or determining the sequences of at least one individual target template nucleic acid molecules.

The term 'target template nucleic acid molecule' refers to a nucleic acid molecule which the operator of the method intends to sequence. A 'template nucleic acid molecule' may comprise part of a larger nucleic acid molecule such as a chromosome. A 'template nucleic acid molecule' may comprise a gene, multiple genes or a fragment of a gene. A 'template nucleic acid molecule' may be isolated using primers which are capable of hybridising to the template nucleic acid molecule.

There are at least two target template nucleic acid molecules in the sample of nucleic acids. In the case of 16S sequencing the at least two target template nucleic acid molecules could include multiple molecules each encoding a different 16S rRNA. For example, the at least two target template nucleic acid molecules could include nucleic acids encoding 16S rRNA from different bacteria, nucleic acids encoding different molecules of 16s rRNA from the same bacterium or both. Alternatively the at least two target template nucleic acid molecules may comprise multiple copies of the same gene. The 'target template nucleic acid molecules' may comprise a fragment of the 16s rRNA, however it is preferable that the fragment is at least 1 Kbp in length. This is because the inventors have demonstrated that when 16S sequencing is used for phylogenetic studies, the longer the strand of 16s rRNA that is sequenced the higher the level of taxonomic resolution that can be obtained.

In one embodiment of the invention the at least one target template nucleic acid molecule is greater than 1 Kbp, greater than 1.2 Kbp, greater than 1.3 Kbp or greater than 1.5 Kbp in size. In a further embodiment of the invention the at least one target template nucleic acid moleculeis less than 100 Kbp, less than 50 Kbp, less than 25 Kbp, less than 15 Kbp, less than 10 Kbp, less than 5 Kbp, less than 3 Kbp or less than 2 Kbp in size.

In a further embodiment of the invention the method is a high throughput method for generating sequences of at least one target template nucleic acid molecule.

Providing at Least One Sample of Nucleic Acids

Some aspects of the invention require a step of providing at least one sample of nucleic acids comprising at least two target template nucleic acid molecules. Optionally the at least two target template nucleic acid molecules are greater than 1 Kbp in size.

In general the term 'comprising' is intended to mean including but not limited to, for example the phrase 'comprising the following steps' indicates that the method includes those steps but that additional steps may also be performed. In some embodiments of the invention the word 'comprising' can be replaced by the word 'consisting'. The term 'consisting' is intended to be limiting, for example if a method is 'consisting the following steps' the method includes those steps and no others.

The sample may be any sample of nucleic acids. The sample of nucleic acids may be a sample of nucleic acids derived from a human, for example a sample extracted from a skin swab of a human patient. Alternatively the sample of nucleic acids may be derived from other sources such as a sample from a water supply. Such a sample could contain billions of template nucleic acid molecules. It would be possible to sequence each of these billions of template nucleic acid molecules simultaneously using the method of the invention thus there is no upper limit on the template nucleic acid molecules which could be used in the method of the invention.

In a further embodiment of the invention the method comprises providing multiple samples of nucleic acids, for example 2, 3, 4, 5, 6, 7, 8, 9, 10, 11, 15, 20, 25, 50, 75 or 100 samples. Optionally less than 100, 75, 50, 25, 20, 15, 11, 10, 9, 8, 7, 6, 5 or 4 samples of nucleic acids provided. In a further embodiment between 2 and 100, 2 and 75, 2 and 50, 2 and 25, 5 and 15 or 7 and 15 samples are provided.

Introducing a First Molecular Tag and a Second Molecular Tag and Amplifying the at Least Two Tagged Template Nucleic Acid Molecules Some of the methods of the invention involve introducing a first molecular tag into one end of each of the at least two template nucleic acid molecules and a second molecular tag into the other end of each of the at least two template nucleic acid molecules to provide at least two tagged template nucleic acid molecules. Some of the methods of the invention involve amplifying the at least two tagged template nucleic acid molecules to provide multiple copies of the at least two template nucleic acid molecules.

In order to allow the template nucleic acid molecules in the sample to be sequenced the template nucleic acid molecules should be amplified optionally by PCR in order to provide multiple copies of each template nucleic acid molecule (i.e. to ensure that the template nucleic acid molecules are at sufficient concentration for the sequencing reaction). In one embodiment the amplification is carried out by polymerase chain reaction (PCR). The amplification step also ensures that the target template nucleic acid molecules are enriched relative to the other nucleic acids in the sample. The amplification step uses primers that hybridise to the target template nucleic acid molecules thus amplifying the target template nucleic acid only and increasing the concentration of the target template nucleic acid molecules relative to the other nucleic acids in the sample (enrichment). However, since samples generally contain multiple target template nucleic acid molecules this amplification step may amplify multiple target template nucleic acid molecules. For example in 16S sequencing, a sample may contain 16S DNA templates from multiple bacteria, the primers used in the amplification step may hybridise to all of these 16S gene sequences and thus all of these DNA templates will be amplified. This can be achieved by using degenerate primers which may vary slightly in sequence such that a group of degenerate primers can hybridise to (or are complementary to) similar but not identical target template nucleic acid sequences.

It is advantageous to be able to determine which of the sequences generated in the sequencing steps originated from the same original template nucleic acid molecule. Accordingly the term 'tagged template nucleic acid molecule' refers to a molecule comprising a 'target template nucleic acid molecule' and a tag at each end. This allows consensus sequences for each molecule of original template nucleic acids to be determined. This can be achieved by adding molecular tags into both ends (the 5' and 3' ends) of each of the original template nucleic acid molecules (Lundberg et al; Nature Methods 10: 999-1002) to produce tagged template nucleic acid molecules. The first and/or second molecular tag will be considered to have been introduced into the ends of the template DNA molecules as long as they are near, in sequence, to the terminal nucleotides (the first or last nucleotide in the sequence) of the template DNA molecules. In one embodiment there are less than 50, 40, 30, 25, 20, 15, 10 or 5 nucleotides between a terminal nucleotide and the first molecular tag. In a further embodiment there are less than 50, 40, 30, 25, 20, 15, 10 or 5 nucleotides between a terminal nucleotide and the second molecular tag.

The methods of the invention require that the first molecular tag and the second molecular tag are unique. In this case the term 'unique' refers to molecular tags which comprise a random sequence of base pairs, assuming that there are enough random nucleotide sequences used each first molecular tag and each second molecular tag will be have a different sequence from every other tag that is generated. However in some embodiments the same tag sequence may occur more than once, in this embodiment the first molecular tag and the second molecular tag will still be considered to be 'unique'. In a further embodiment each first molecular tag and each second molecular tag comprise nucleotide sequences which are different to the nucleotide sequences of every other first molecular tag and second molecular tag. In a further embodiment at least 90% of the first molecular tags and the second molecular tags comprise nucleotide sequences which are different to the nucleotide sequences of every other first molecular tag and second molecular tag. This means that sequences of nucleic acid molecules sharing the same pair of first and second unique molecular tags are likely to have originated from the same original template nucleic acid molecule (birthday paradox). In addition sequences of fragments of nucleic acid comprising either the first molecular tag or the second molecular tag associated with a target template nucleic acid molecule are also likely to have originated from that target template DNA molecule. The use of two unique molecular tags also allows for sequences that are generated by recombination during the methods of the invention to be identified and disregarded.

The first molecular tag and the second molecular tag sequences may also comprise a few nucleotides from the target template nucleic acid sequence, for example less than 50, 40, 35, 30, 25, 20, 15 or 10 base pairs of the target template nucleic acid molecule sequence.

In one embodiment the first molecular tag and the second molecular tag are greater than 5 bp, greater than 6 bp or greater than 7 bp in size. In a further embodiment the first molecular tag and the second molecular tag are less than 20 bp, less than 18 bp, less than 15 bp, or less than 10 bp in size.

Such unique molecular tags can be introduced using a variety of techniques including PCR, tagmentation and physical shearing or restriction digestion of target nucleic acids combined with subsequent adapter ligation (optionally sticky-end ligation). For example PCR can be carried out on the at least two target template nucleic acid molecules using a first set of primers capable of hybridising to (optionally complementary to) the at least two target template nucleic acid molecules. In one embodiment of the invention the first molecular tag and the second molecular tag are introduced into each of the at least two template nucleic acid molecules by PCR using primers comprising a portion (a 5' end portion) comprising the first molecular tag or the second molecular tag and a portion (a 3' end portion) having a sequence that is capable of hybridising to (optionally complementary to) the at least two target template nucleic acid molecules. Such primers will hybridise to target template nucleic acid molecule, PCR primer extension will then provide a nucleic acid molecule which comprises either the first molecular tag or the second molecular tag. A further round of PCR with these primers will provide tagged template nucleic acid molecules comprising a first molecular tag at one end and a second molecular tag at the other end. In a further embodiment the primers are degenerate, i.e. the 3' end portion of the primers are similar but not identical to one another. For example, if the method of the invention is used for 16S ribosomal sequencing the 3' end portion of the primers may vary slightly primer to primer but each 3' end portion will be complementary to the 16S sequence in at least one organism. This allows sequencing of a 16S sequence whose origin is unknown, thus enabling sequencing of any 16S rRNA sequence irrespective of its origin (for example the bacterium from which it is derived). Such sequences can then be used in phylogenetic studies. In an embodiment where the at least two target template nucleic acid molecules are 16S rRNA genes, suitable primers may have a 3' end portion comprising the 27F (Weisberg et al, J Bacteriol. 1991 January; 173(2): 697-703) or 1391R (Turner et al, 1999) bacterial primer sequences.

In a separate embodiment of the invention the first molecular tag and the second molecular tag can be introduced using tagmentation. In an embodiment wherein the first molecular tag and the second molecular tag are introduced using tagmentation they can be introduced using direct tagmentation, or by introducing a defined sequence by tagmentation followed by two rounds of PCR using primers that comprise a portion capable of hybridising to the defined sequence and a portion comprising the first molecular tag or the second molecular tag. In a further embodiment of the invention the first molecular tag and the second molecular tag can be introduced by restriction digestion of the original nucleic acids followed by ligation of nucleic acids comprising the first or second molecular tag. The restriction digestion of the original nucleic acids should be performed such that the digestion results in a molecule comprising the region to be sequenced (the at least one target template nucleic acid molecule).

In an embodiment where the first molecular tag and the second molecular tag are introduced into the at least two target template nucleic acid molecules by PCR, the primers used may comprise a further portion comprising a constant 'stub sequence'. This constant stub sequence is preferably 5' of the unique molecular tag. In this embodiment the tagged template nucleic acid molecules provided will further comprise a stub sequence.

In an embodiment where multiple samples of nucleic acids are provided, the method comprises a further step of introducing a sample barcode into one of the ends of the target template nucleic acid molecules in each sample. This further step occurs before or during the step of introducing a first molecular tag into one end and a second molecular tag into the other end of each of the at least two target template nucleic acid molecules in the methods of the present invention. These sample barcodes may be introduced in a similar way to introducing the first molecular tag and the second molecular tag, for example a round of PCR may be carried out on each sample separately in which the primers used hybridise to (or are complementary to) the at least two target template nucleic acid molecules and comprise a portion (optionally a 3' portion) which comprises the sample barcode. Optionally in an embodiment where the first molecular tag and the second molecular tag are introduced into the at least two template nucleic acid molecules by PCR, the primers used to introduce the tags may comprise a further portion comprising a sample specific barcode. In this embodiment a first round of PCR is carried out on each sample of nucleic acids separately. The first round of PCR may use primers comprising the first molecular tag or the second molecular tag, a sample specific barcode which is identical for every nucleic acid template molecule in the sample, a region which hybridises to the template nucleic acid molecules and optionally a stub region. The samples of nucleic acids can then be pooled and subject to further rounds of PCR using primers (optionally which are capable of hybridising to or are complementary to the 'stub' region) which do not comprise a sample specific barcode. Optionally a second round of PCR is carried out using a primer which comprises a second sample specific barcode, in this embodiment the samples of nucleic acids are not pooled until after the second round of PCR.

The step of amplifying the at least two tagged template nucleic acid may involve PCR using a second set of primers which are capable of hybridising with the ends of the tagged template nucleic acid molecules in such a way that primer extension will result in multiple copies of the tagged template nucleic acid molecules and will maintain the first molecular tag and the second molecular tag. In an embodiment where the first set of primers comprises a stub sequence, the second set of primers may comprise a region which is capable of hybridising to the stub sequence of the tagged template nucleic acid molecules.

Isolating a Fraction of the Amplified Template Nucleic Acid Molecules and Fragmenting the Amplified Template Nucleic Acid Molecules in the Fraction The method may comprise isolating a fraction of the amplified template nucleic acid molecules and fragmenting the amplified template nucleic acid molecules in the fraction to provide multiple fragmented template nucleic acid molecules.

By the term 'fragment' we are referring to a short segment of a nucleic acid molecule i.e. to a string of nucleotides which form part of a 'full length' sequence. Fragments according to the invention will be at least 10, 15, 20, 50, 100, 200, 250 or 500 base pairs long. Optionally fragments according to the invention will be less than 2500, 2200, 2000 or 1500 base pairs long.

Fragmentation can be carried out using any appropriate method. For example, fragmentation can be carried out using restriction digestion or using PCR with primers complementary to at least one internal region of the tagged template nucleic acid molecules. Preferably fragmentation is carried out using a method that produces arbitrary fragments. The term "arbitrary fragment" refers to a randomly generated fragment, for example a fragment generated by tagmentation. Fragments generated using restriction enzymes are not "arbitrary" as restriction digestion occurs at specific DNA sequences defined by the restriction enzyme that is used. Even more preferably fragmentation is carried out by tagmentation. If fragmentation is carried out by tagmentation, the tagmentation reaction optionally introduces an adapter region into the fragmented template nucleic acid molecules. This adapter region is a short DNA sequence which may encode, for example adapters to allow the fragmented template nucleic acid molecules to be sequenced using Illumina MiSeq technology.

In a typical embodiment this step may comprise a further step of enriching the multiple fragmented template molecules to increase the proportion of the multiple fragmented template nucleic acid molecules comprising the first molecular tag or the second molecular tag. In this preferred embodiment the step of enriching the multiple fragmented template nucleic acid molecules is preferably carried out by PCR. Preferably the PCR is carried out using primers which are capable of hybridising to (optionally complementary to) either the first or second molecular tag and primers which are capable of hybridising to (optionally complementary to) internal regions of the at least two tagged template nucleic acid molecules. Such a PCR step will increase the concentration of fragments comprising the first molecular tag or the second molecular tag.

In an embodiment where fragmentation is carried out by tagmentation and the tagmentation introduces an adapter region into the fragmented template nucleic acid molecules, enrichment may be carried out by PCR using primers that are capable of hybridising to (optionally complementary to) either the first or second molecular tag and primers that are capable of hybridising to (optionally complementary to) the adapter sequence.

Sequencing Regions of the at Least Two Tagged Template Nucleic Acid Molecules and/or Sequencing the Multiple Fragmented Template Nucleic Acid Molecules In general sequencing steps can be carried out using any method of sequencing. Examples of possible sequencing methods include Maxam Gilbert Sequencing, Sanger Sequencing, or sequencing comprising bridge PCR. In a typical embodiment the sequencing steps involve bridge PCR, optionally the bridge PCR step is carried out using an extension time of greater than 5, 10, 15 or 20 seconds. An example of the use of bridge PCR is in Illumina Genome Analyzer Sequencers.

The method of the invention may comprise a step of sequencing regions of the at least two tagged template nucleic acid molecules. As described above, the method of the invention requires that a first and a second molecular tag are introduced into the at least two target template nucleic acid molecules and that each of the at least two template nucleic acid molecules is tagged with a unique tag. Since each of the tagged at least two template nucleic acid molecules comprises a unique tag then, even though multiple copies of the at least two template nucleic acid molecules are produced after the amplification step, it is possible to see which sequences correspond to which individual target template nucleic acid molecule. In order to achieve this the operator must be able to determine the sequence of the first and second unique molecular tag associated with each original target template nucleic acid molecule. This is achieved by sequencing regions of the at least two tagged template nucleic acid molecules wherein the regions comprise the first molecular tag and the second molecular tag. This step may comprise sequencing the entire length of the at least two tagged template nucleic acid molecules or typically comprises sequencing only the ends of the at least two tagged template nucleic acid molecules.

The method of the invention may comprise a step of sequencing multiple fragmented template nucleic acid molecules. In an embodiment wherein the method comprises a step of sequencing multiple fragmented template nucleic acid molecules, this can be performed in the same sequencing run as the sequencing run in which the at least two tagged template nucleic acid molecules are sequenced. On the other hand it can be more efficient and accurate to sequence the multiple fragmented template nucleic acid molecules in a separate sequencing run from the at least two tagged template nucleic acid molecules.

Reconstructing a Consensus Sequence for at Least One of the at Least Two Template Nucleic Acid Molecules The methods of the invention may comprise a step of reconstructing a consensus sequence for at least one of the at least two template nucleic acid molecules.

Optionally the step of reconstructing a consensus sequence comprises a step of identifying clusters of sequences of multiple copies of the at least two tagged template nucleic acid molecules which are likely to correspond to the same template nucleic acid molecule by assigning sequences comprising first molecular tag sequences which are homologous to one another and second molecular tag sequences which are homologous to one another to the same cluster (for example step S2). For the purposes of the present invention the phrase "homologous to one another" requires that two sequences have greater than 75%, 80%, 85%, 90%, 95%, 98%, 99% or 100% sequence identity to one another over the whole length of the longest sequences. For example if the sequences comprise molecular tags of 10 bp, two molecular tags will be 90% identical to one another if the tags differ in only one base pair. This difference can be a replacement or a deletion of a base pair. This can be determined by aligning the sequences of the molecular tags and comparing them using the 'uclust' algorithm or any similar sequence clustering algorithm such as CD-HIT.

Optionally the step of reconstructing a consensus sequence comprises a step of analysing the sequences of the at least two tagged template nucleic acid molecules and/or the multiple fragmented template nucleic acid molecules to identify sequences of the at least two tagged template nucleic acid molecules and/or multiple fragmented template nucleic acid molecules which comprise a first molecular tag or a second molecular tag which is homologous to the first molecular tag or the second molecular tag of the sequences of a first cluster (for example step S4 or S7). This may comprise a step of determining a consensus sequence for the first molecular tag sequence and the second molecular tag sequence of a cluster. As described above sequences will be assigned to the same cluster if the first molecular tag sequences and the second molecular tag sequences are homologous to one another. The first molecular tag and the second molecular tag sequences may be slightly different to one another even where the sequences have originated by the same individual target template nucleic acid molecule due to errors in the sequence introduced during the method of the invention. Thus a consensus sequence from these homologous first molecular tag and second molecular tag sequences can be defined. This consensus sequence is highly likely to represent the sequence of the tag as it was introduced into the target template nucleic acid molecule. Once a consensus sequence for the first molecular tag and the second molecular tag for a cluster have been defined sequences of the multiple fragmented template nucleic acid molecules which comprise a first molecular tag or a second molecular tag which is homologous to one of these consensus sequences can be identified. This provides greater accuracy in identifying the multiple fragmented template nucleic acid molecules which correspond to a particular original template nucleic acid molecule.

As described above each tagged template nucleic acid molecule comprises a first molecular tag and a second molecular tag. These tagged template nucleic acid molecules are copied and the copies fragmented. Each fragment will have the same sequence as a portion of the individual target template nucleic acid molecule (notwithstanding the possibility of some error in replication during PCR amplification steps) and thus can be considered to 'correspond' to a portion of the original individual target template nucleic acid molecule. A portion of these fragments will comprise the first molecular tag or the second molecular tag. Once sequenced it can, therefore, be identified which individual target template nucleic acid molecule the fragment corresponds to.

Optionally the step of reconstructing a consensus sequence comprises a step of reconstructing the sequence of a first template nucleic acid molecule by aligning at least a subset of the sequences of the multiple fragmented template nucleic acid molecules identified as comprising a first molecular tag or a second molecular tag homologous to the first molecular tag or the second molecular tag of the sequences of the first cluster and defining a consensus sequences from these sequences (for example step S4, S6 or S7).

As described above the nature of the first molecular tag or second molecular tag associated with each fragment allows the operator to determine which original template nucleic acid molecule the fragment corresponds to. There will be multiple fragments produced corresponding to the same original template nucleic acid molecule. The sequences of each one of these fragments will correspond to a different (potentially overlapping) region of the template nucleic acid molecule. The sequence of the template can be reconstructed by aligning these fragments and calculating a consensus sequence from the aligned fragments. The term 'aligning' refers to arranging the sequences of the fragments in such a way as to align areas of the sequences sharing a common sequence. This can be carried out using software such as Clustal W2, IDBA-UD or SOAPdenovo. Once the sequences are aligned the consensus sequence can be determined. As described above, during the sequencing reaction, mutations may be introduced into the sequences, however these mutated sequences will be at a lower concentration than the accurate sequences. For this reason a 'consensus sequence' is defined. The term 'consensus sequence' can, in the context of the present invention be considered to refer to the most likely sequence for at least one individual target template nucleic acid molecule when considering the sequence of all fragments corresponding to that at least one template nucleic acid molecule.

In one embodiment each of the sequences of the multiple fragmented template nucleic acid molecules which were identified as comprising a first molecular tag or a second molecular tag homologous to the first molecular tag or the second molecular tag of the sequences of the first cluster are aligned and used to define the consensus sequence (the consensus sequence that is defined does not comprise the first molecular tag or the second molecular tag). In a further embodiment at least a subset but not all of the identified multiple fragmented template nucleic acid molecule sequences are aligned and used to define the consensus sequence. In a further embodiment 90%, 92%, 95%, 98%, 99% or 100% of the identified multiple fragmented template nucleic acid molecule sequences are aligned and used to define the consensus sequence. In a further embodiment the sequences of the full length at least one tagged template nucleic acid molecule are also included in the alignment and used to define the consensus sequence.

Optionally the method of the invention comprises performing the steps required to reconstruct a consensus sequence for a second or further template nucleic acid molecule. Generally this will involve repeating steps for a second cluster of sequences having first molecular tags that are homologous to one another and second molecular tags that are homologous to one another.

Optionally these steps of reconstructing a consensus sequence for at least one of the target template nucleic acid molecules are performed by a computer. In a further aspect of the invention there is provided a computer program capable of carrying out these steps of reconstructing a consensus sequence for at least one of the target template nucleic acid molecules optionally stored on a computer-readable medium.

Disregarding Sequences of Recombination Products

In an aspect of the present invention there is provided a method for generating sequences which comprises or further comprises selecting at least one cluster of sequences wherein the sequences within the selected clusters comprise a first molecular and a second molecular tag which are more commonly associated with one another (e.g. at least 2 times, at least 5 times, at least 8 times or at least 10 times more commonly) than with a different first molecular tag or second molecular tag.

Optionally this step of selecting at least one cluster consists of identifying groups of clusters of sequences of the at least two tagged template nucleic acid molecules wherein the sequences within the clusters of each group have first molecular tags which are homologous to one another or identifying groups of clusters of sequences of the at least two tagged template nucleic acid molecules wherein the sequences within the clusters of each group have second molecular tags which are homologous to one another. Such a method may further comprise selecting a cluster from a group of clusters of sequences wherein the cluster that is selected contains the highest number of sequences; wherein the sequence of the first template nucleic acid molecule is reconstructed from the sequences in the cluster that was selected. This allows products of recombination to be detected. Such recombination can result in nucleic acid molecules comprising a sequence corresponding to one part of an original template nucleic acid molecule and a sequence corresponding to one part of a different original template nucleic acid molecule being produced. However such recombination products can be detected if first and second unique molecular tags are introduced into the template nucleic acid molecules. If a recombination event occurs the pair of unique molecular tags will not be the same as any of the pairings of unique molecular tags on any of the original tagged template nucleic acid molecules. This means whilst one might expect one single cluster of sequences to be identified where all the sequences comprise the same first molecular or second molecular tags, if a small amount of recombination has taken place there may be more than one cluster having the same first molecular tag, but pairing this first molecular tag with at least two different second molecular tags. However, these clusters will contain fewer sequences than the cluster which has the same pair of first molecular and second molecular tags as the original template nucleic acid molecule, as a smaller number of copies of the products of recombination will tend to be present than the original template nucleic acid.

Indeed, it is possible to use the methods of the invention to determine the rate at which recombination is occurring (or the number of recombinants that are generated in a sequencing process). For example, clusters can be identified comprising sequences having a first molecular tag and a second molecular tag which are most commonly associated with one another. Other clusters comprising sequences having the same first molecular tag but a different second molecular tag or the same second molecular tag but a different first molecular tag are likely the result of recombination events and these clusters may be referred to as recombination product clusters. The numbers of sequences in these recombination product clusters may be quantified. The proportion of these sequences (that are the result of recombination) compared to the total number of sequences may be calculated.

A method of the invention may comprise steps of:
a) providing at least one sample of nucleic acid molecules comprising at least two target template nucleic acid molecules;
b) introducing a first molecular tag into one end of each of the at least two target template nucleic acid molecules and a second molecular tag into the other end of each of the at least two target template nucleic acid molecules to provide at least two tagged template nucleic acid molecules wherein each tagged template nucleic acid molecule is tagged with a unique first molecular tag and a unique second molecular tag;
c) amplifying the at least two tagged template nucleic acid molecules to provide multiple copies of the at least two tagged template nucleic acid molecules; d) sequencing regions of the at least two tagged template nucleic acid molecules comprising the first molecular tag and the second molecular tag; and
e) identifying and disregarding sequences that are the product of recombination events.

Step e) may comprise a step of identifying clusters of sequences of multiple copies of the at least two tagged template nucleic acid molecules which are likely to correspond to the same template nucleic acid molecule by assigning sequences comprising first molecular tag sequences which are homologous to one another and second molecular tag sequences which are homologous to one another to the same cluster. Step e) may further comprise selecting clusters of sequences wherein the sequences within the selected clusters comprise a first molecular and a second molecular tag which are more commonly associated with one another than with a different first molecular tag or second molecular tag. Step e) may further comprise disregarding any sequences that are not present within one of these selected clusters.

Optionally such a method further comprises a step of determining a consensus sequence from one of the selected clusters. This method may also comprise a step f) of determining the rate at which recombination occurs or the percentage of the total amount of DNA that is a result of a recombination event. In order to perform such a step f), one should determine the total number of sequences present, and the number of sequences that have been disregarded. The percentage of the total DNA that is a result of a recombination event will be equal to the number of sequences that have been disregarded/the total number of sequences×100. When generating a consensus sequence, the estimated recombination rate for the cluster can be applied to remove reads that diverge from the majority consensus where the divergent sequence occurs at the rate expected for recombinant fragments. Typically, a sequence that occurs at one of the following frequencies may be disregarded: less than 30%, less than 20%, less than 15%, less than 12% or less than 11%. The estimated recombination rate for a cluster can be reported as a quality metric for the sequence.

Methods for Determining a Sequence of at Least One Template Nucleic Acid Molecule The invention further provides methods for determining sequences of at least two template nucleic acid molecules.

In such a method data is obtained/input (S1, S3 or S5), for example data comprising sequences of at least two template nucleic acid molecules and/or the data comprising sequences of regions of the at least two template nucleic acid molecule comprising the first molecular tag and the second molecular tag, can be obtained using the method steps described above.

In a particular embodiment this method is performed by a computer. In a further aspect there is provided a computer program adapted to perform the methods of the invention when the program is run on an electronic device. In a further aspect there is provided a computer readable medium storing the computer program of the invention.

Figure 8:
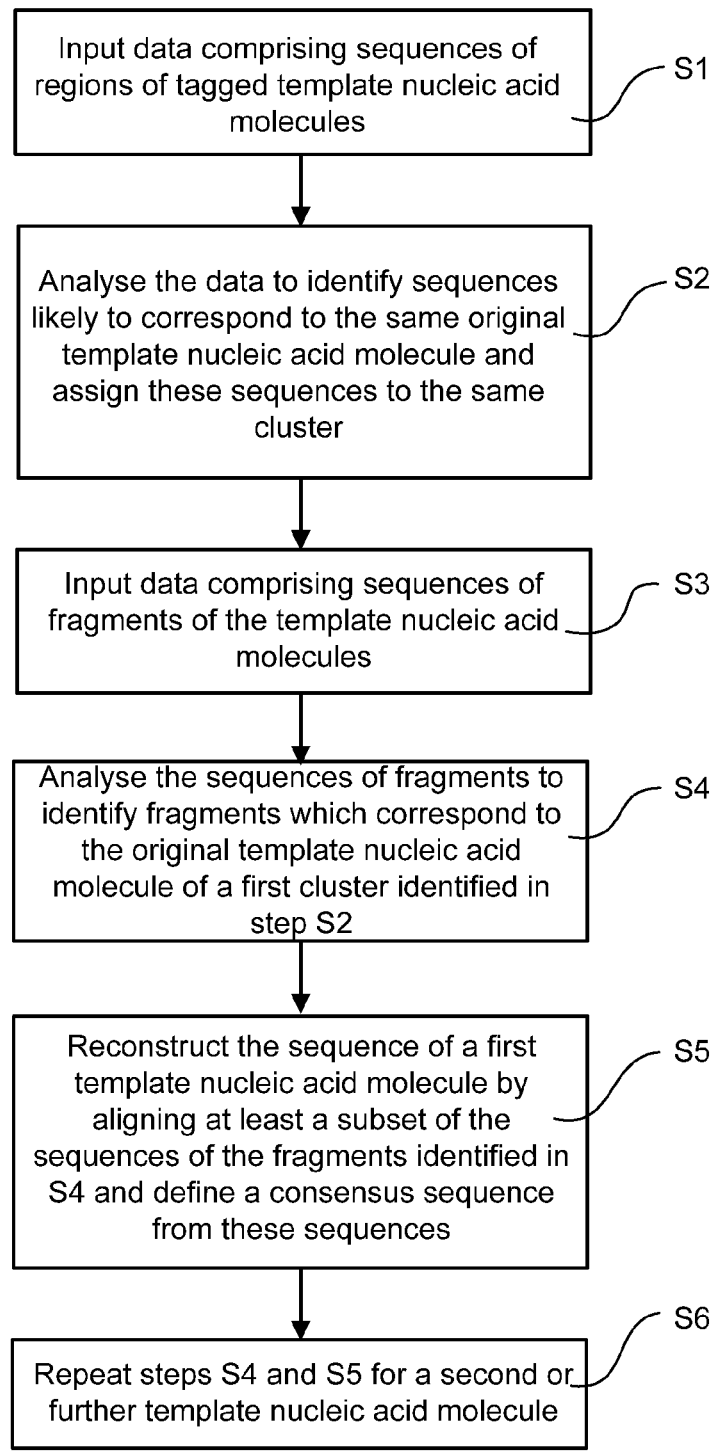
FIGS. 8-11. Flow charts depicting methods of the invention
Figure 9:
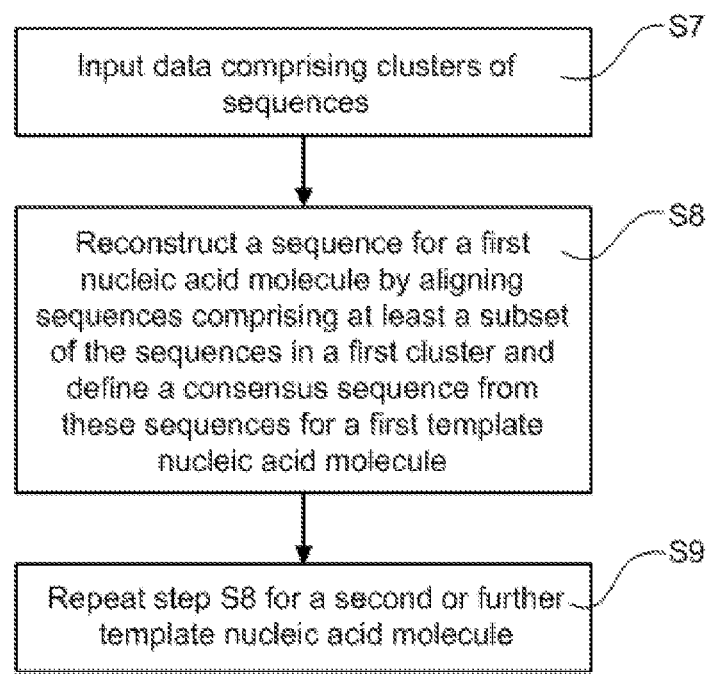
Figure 10:
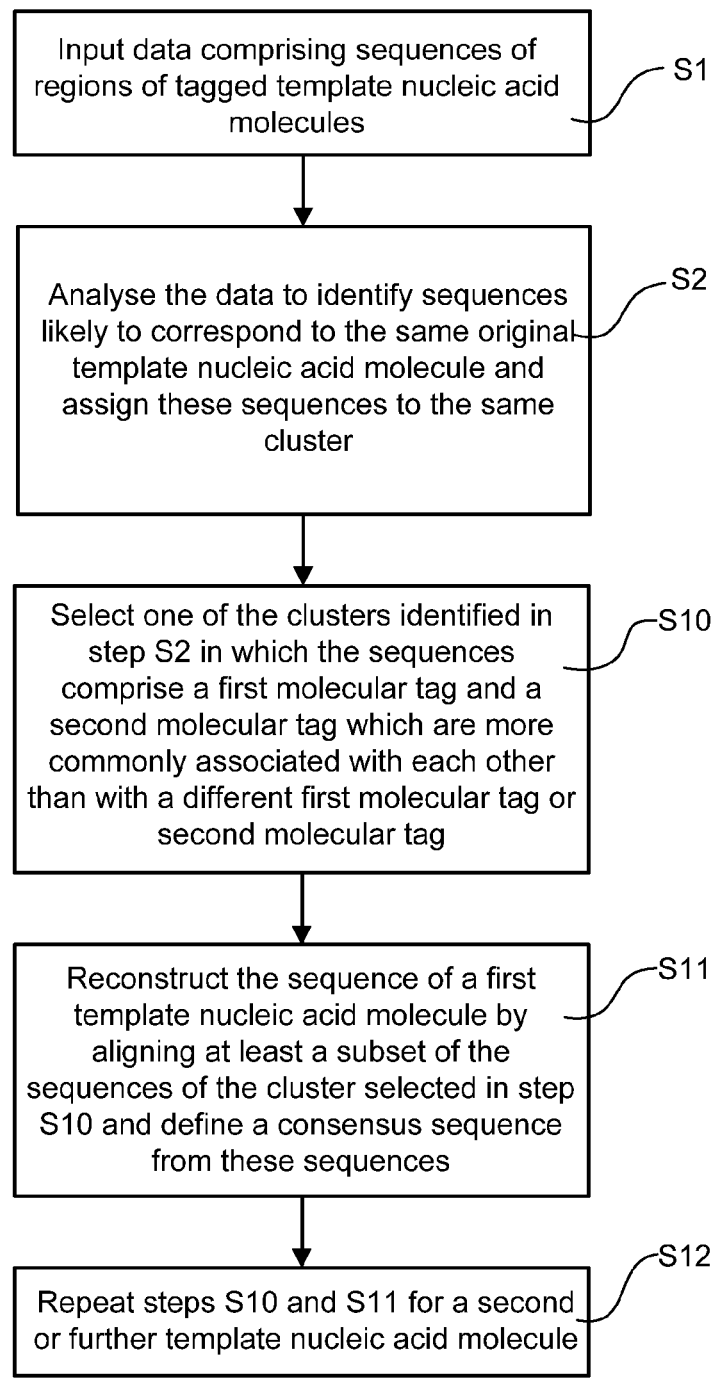
Figure 11:
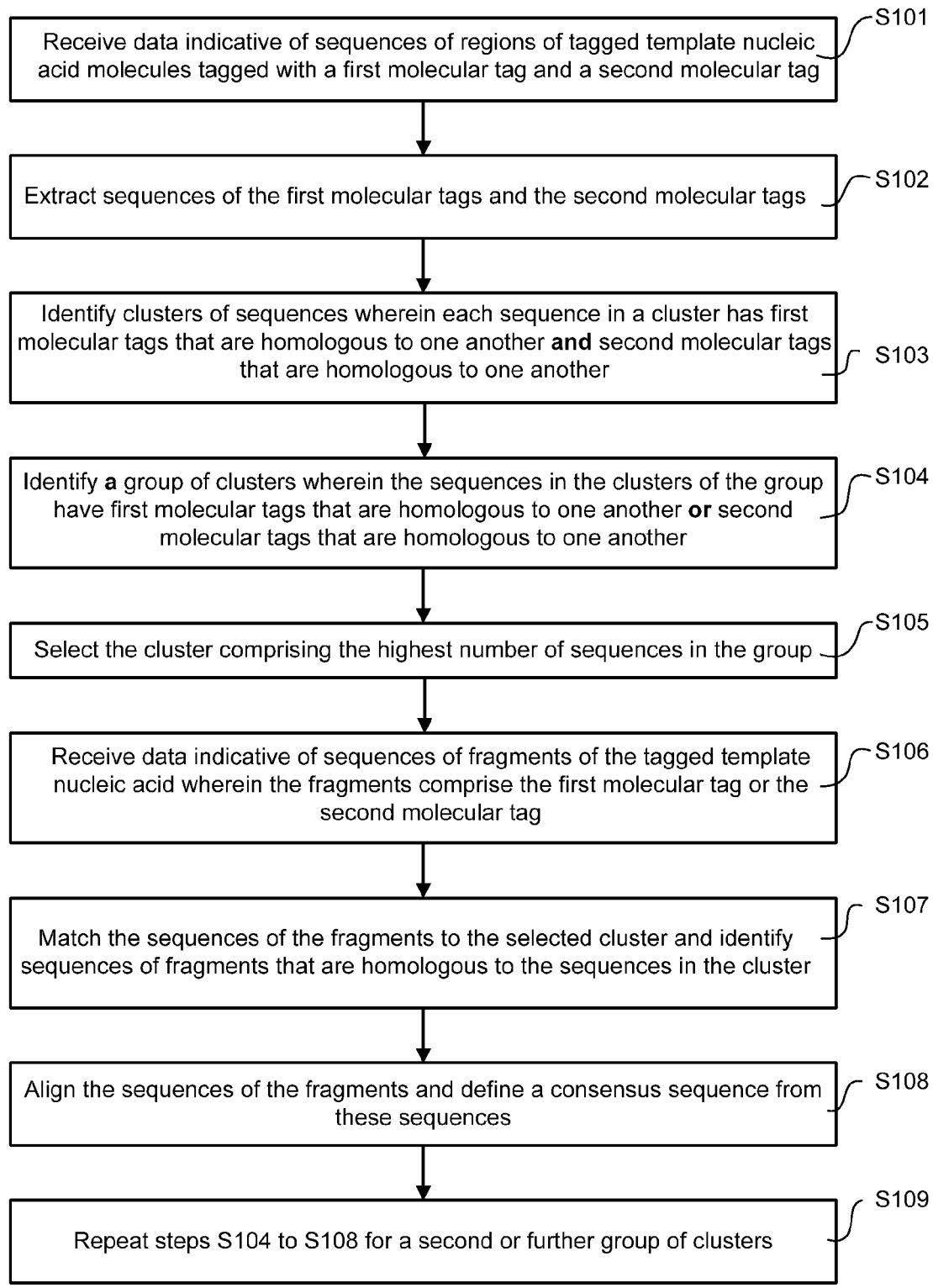

As discussed, aspects of the methods discussed herein, including the methods illustrated in FIGS. 8 to 11, can be implemented by a computer. It is well known that an individual computer can comprise standard hardware elements such as CPUs, RAM, storage devices, etc. It is also well known that pluralities of computers can be connected together and can cooperate so as to perform computing tasks collectively (as a distributed processing system). It will therefore be appreciated that references to computer-implemented methods is intended to include, but not be limited to, methods that use a data processing system (computer) that can perform one or more of the steps described independently or a distributing processing system. A desktop PC working with a cloud computing system via an internet connection is an example of a distributed processing system. Referring to FIG. 8, for example, the data to be input in steps S1 and S3 could be stored at a central server in a cloud computing system (this may be referred to as a cloud storage system) and accessed by a desktop computer that is configured to perform the analysis steps S2, S4 and S5. Alternatively, the data to be input in steps S1 and S3 could be provided by the desktop computer and the cloud computing system could be configured to perform the analysis steps S2, S4 and S5 and return the results to the desktop computer. It will be appreciated any other distribution of the data storage and data processing tasks between different computers could be adopted according to the needs of a particular application.

Further Developments

Methods of the invention can be modified for even longer sequences. For example, in a method comprising fragmenting the template nucleic acid molecules a further step of introducing further molecular tags (for example a third and a fourth molecular tag) into the fragmented template nucleic acid molecules can be performed. This allows for the fragmented template nucleic acid molecules to be fragmented further, and the further fragmented template nucleic acid molecules to be sequenced. The use of a third molecular tag and a fourth molecular tag allows for reconstructing the sequence of the full length sequence from the further fragmented template nucleic acid molecules.

The methods of the invention may be used to sequence multiple different genes within a sample of nucleic acids. For example the method of the invention could be used to sequence the whole or a large proportion of the genome of an organism of interest such as a medically relevant pathogen by using a range of primers capable of hybridising to nucleic acids comprising multiple genes. In one embodiment these primers are tethered to a solid surface or coupled to a selectable marker such as biotin.

Kits

In a some aspects of the invention kits are provided. Optionally these kits comprise one or more of the following:

(i) primers comprising a portion comprising a first molecular tag or a second molecular tag and a portion having a sequence that is capable of hybridising to a target template nucleic acid molecule; optionally wherein the primers comprise a 'stub region';

(ii) primers comprising a portion capable of hybridising to the primers of (i), for example primers comprising a region complementary to the 'stub region';

(iii) a component capable of fragmenting a target template nucleic acid molecule for example a transposase, restriction enzymes or further primers which are complementary to internal regions of the target template nucleic acid molecule;

(iv) primers comprising a portion capable of hybridising to a fragmented target template nucleic acid molecule;

(v) reagents for performing amplification, for example by polymerase chain reaction;

(vi) instructions describing how to perform the methods of the invention; and/or (vii) a computer readable medium storing a computer program of the invention.

EXAMPLE 1

Extraction of Microbial DNA from Foot Skin

DNA was extracted from skin swabs taken from the feet of 6 different healthy individuals. 12 samples were taken in total. Skin swabs were collected by swabbing either the ball or heel area of the left or right foot with a rayon swab moistened in a solution of 0.15 M NaCl and 0.1% Tween 20. The swab was rubbed firmly over the skin for approximately 30 seconds. Swab heads were cut into bead beating tubes, and DNA was extracted from the swabs using the BiOstic Bacteriemia DNA Isolation Kit (Mo-Bio), as per the manufacturers instructions. DNA was quantified on a Qubit with a dsDNA HS assay (Life Technologies).

EXAMPLE 2

Preparation of Short Read 16S Libraries for Illumina Sequencing

A library of the V4 region of the 16S gene was prepared for Illumina sequencing from the microbial foot skin DNA samples using a previously published method (Caporaso et al, 2012, ISME 6(8)). Briefly, samples were amplified using primers based on the Caporaso design, which were modified to include 8 bp rather than 12 bp sample barcodes, and include a barcode on both the forward and reverse primer (primer sequences are described in FIG. 2). The V4 region was amplified from 500 pg template DNA using 10 cycles of PCR with the modified Caporaso primers (Caporaso_forward and Caporaso_reverse), using different barcoded primers for each sample. After removal of excess primer via a magnetic bead clean-up (Agencourt) samples were pooled, and subjected to a further 20 cycles of PCR to enrich for amplicons containing the Illumina adaptors, using primers Illumina_E_1 and Illumina_E_2 (see FIG. 2 for details of primers). PCRs were carried out with a Taq core PCR kit (Qiagen), under the conditions described in Caporaso et al, (2012, ISME 6(8)). Amplicons were sequenced using a nano flow cell and a 500 cycle V2 kit on an Illumina MiSeq, following the method described in Caporaso et al (2012, ISME 6(8)). This method will be referred to as "short sequencing" and data produced with this method as "V4" data, from here-on in.

EXAMPLE 3

Preparation of Full Length 16S Libraries for Illumina Sequencing with Unique Molecular Tags Primers for amplification of the 16S gene contained the 27F (Weisberg et al, *J Bacteriol.* 1991 January; 173(2): 697-703) or 1391R (Turner et al, Journal of Eukaryotic Microbiology, 1999, 46: 327-338) bacterial primer sequences, an 8 bp barcode sequence, a 10 bp unique molecular tag and partial Illumina PE adapter sequences. Primer sequences (Long_forward and Long_reverse) are shown in FIG. 2. The use of a 10 bp unique molecular tag on both forward and reverse primers (10 billion possible unique tags at each end) allowed us to uniquely tag each 16S molecule in our pool, using a method similar to Lundberg et al (Nature Methods, 2013, 10: 999-1002). Template DNA was subject to one cycle of PCR with the forward primer, followed by a bead clean-up to remove excess primer, then another cycle of PCR with the reverse primer, followed by another bead clean-up. The first PCR carries out extension of the 16S gene from the forward primer, which introduces unique molecular tags into each different 16S template molecule in the reaction. The second PCR uses the extension products from the first PCR as a template, and produces molecules with unique molecular tags at both ends. While the original 16S molecules may also act as a template in the second PCR reaction, these products will only contain a partial Illumina PE adapter sequence at one end, and will therefore not be amplified in the enrichment PCR. The enrichment PCR (34 cycles) amplifies the tagged 16S molecule pool, using primers that are complementary to the partial Illumina PE adapter sequences at the ends of each tagged 16S molecule (Illumina primers PE_1 and PE_2, FIG. 2).

PCRs were carried out using the Taq PCR core kit (Qiagen). Reactions were 50 µl and contained approximately 500 pg DNA template, 0.25 µM F primer, 250 µM dNTPs, 1× PCR buffer, 1× Q solution, and 1.25 U Taq polymerase. PCR cycle conditions were 95° C. for 1 minute, 50° C. for 2 minutes then 72° C. for 3 minutes. This allows extension of the 16S gene from the forward primer, which introduces unique molecular tags into each 16S molecule in the reaction. PCR reactions were then subject to a magnetic bead clean-up using Agencourt SPRI beads as follows. PCR reactions were mixed with 0.6 volume of beads by pipetting, and incubated at room temperature for 1 minute. Tubes were placed on a magnetic rack for 3 minutes to allow the beads to concentrate on the side of the tube, and the supernatant was removed. The beads were washed with 200 µl of 85% ethanol for 30 seconds, after which the ethanol was removed and the beads allowed to air dry for 5 minutes. Once dry the tubes were removed from the magnetic rack, and the beads resuspended in 35 µl nuclease free water by pipetting. After an incubation of one minute at room temperature, tubes were placed back on the magnetic rack for 3 minutes, followed by removal of the DNA containing solution to a new tube. The second PCR was set up as described above, except that 0.25 µM of the reverse primer was used, and the template was 31 µl of the bead-cleaned first round PCR reaction. The PCR cycle applied was 95° C. for 1 minute, 50° C. for 2 minutes and 72° C. for 3 minutes. During this second PCR, the uniquely tagged extension products from the first PCR act as the template, to produce 16S molecules with unique molecular tags on both ends. The second PCR was followed by another magnetic bead clean-up, as described above, and the output of this step was used as a template for the final PCR reaction. The final PCR reaction was set up in a 50 µl volume, and contained 0.5 µM both PE_1 and PE_2 primers (see FIG. 2), 250 µM dNTPs, 1× PCR buffer, 1× Q solution, 31 µl template (from the second bead clean-up) and 1.25 U Taq polymerase. PCR cycling conditions were 95° C. for 2 minutes, followed by 34 cycles of 95° C. for one minute, 58° C. for 30 seconds, and 72° C. for 2 minutes. This was followed by a final extension of 72° C. for 5 minutes. PCRs were again subject to a bead clean-up as described above, before being analysed using a high-sensitivity DNA chip on a Bioanalyser (Agilent).

EXAMPLE 4

Tagmentation of Full Length, Tagged 16S PCR Products

The uniquely tagged, full length 16S PCR amplicons were subject to tagmentation The tagmentation procedure utilises a transposase to simultaneously fragment the DNA while adding an adapter sequence for use on the Illumina platform. Tagmentation was carried out using the Nextera-XT kit as per the manufacturers instructions, with the exception of the PCR amplification step. Here, we carried out two PCRs per tagmentation reaction, each with a combination of one of the Illumina provided PCR primers with one of the primers from the extension PCR above, so as to amplify only those fragments of interest. We aimed to produce a pool of DNA fragments with either the PE_1 (5' end of the coding sequence of the 16S amplicons) or PE_2 (3' end of the coding sequence of the 16S amplicons) sequences on one end, and the i7 or i5 Illumina adaptors (added during the tagmentation reaction) at the other end, respectively (FIG. 2). This provided a pool of fragments from across the 16S gene, which along with the full length 16S amplicons, can be sequenced from either end on the MiSeq. Sequences originating from the same template molecule can be identified via the unique molecular tags at either end of the molecule and re-assembled to provide full length 16S sequences. PCR products from the tagmentation reaction were initially cleaned using 1.8 V of Ampure SPRI beads according the manufacturer's instructions, and in subsequent tagmentation reactions using 0.6 V beads to remove fragments smaller than 400 bp.

EXAMPLE 5

Sequencing of Full Length and Tagmented 16S Amplicons on the Illumina MiSeq

The molarity of both full length 16S tagged amplicons and the tagmentation products was measured via a Bioanalyser High sensitivity DNA chip. During the first sequencing run, only tagmentation products (cleaned with 1.8 V Ampure SPRI beads) were loaded at an average concentration of 1.5 pM and sequenced with a MiSeq reagent kit v2 with 2×150 bp paired end reads, on a nano flow cell. For the second sequencing run, full length 16S tagged amplicons were combined with the tagmentation products (cleaned with 0.6 V Ampure SPRI beads to remove fragments <400 bp) at a ratio of 1:9. The pooled sample was loaded at an average molarity of 6 pM, and sequenced with a MiSeq reagent kit v2 with 2×250 bp paired end reads, on a nano flow cell.

When the full length 16S tagged amplicons were run, modifications were made to the running conditions of the MiSeq. The Chemistry.xml file in the Recipe folder on the Illumina MiSeq contains the protocol used by the instrument for clustering and sequencing DNA fragments. That Chemistry.xml file corresponding to the Illumina Version 2 sequencing kits was modified to increase the "WaitDuration" in the "Amplification 1" "Resyntheses" and "First extension" steps to 15 seconds. This resulted in a process that allowed the ends of individual full length 16S tagged amplicons to be sequenced.

EXAMPLE 6

Reconstructing Full Length 16S Sequences from Tagged Illumina Reads

Sequencing produces data from two kinds of fragments, those which span the entire 16S gene (end+end fragments) and those which pair one end of the 16S gene with a region in the middle of the 16S gene (end+internal fragments). Sequences from end+end fragments encode a pairing of random barcodes and sample barcodes.

To assign sequences to samples, the 8 nt sample barcode region is matched against the collection of known sample barcodes with up to one mismatch tolerated. Because internal regions of the 16S sequence might match a sample barcode, all reads with a potential sample barcode match are then screened for the presence of the proximal or distal 16S primer annealing sequence downstream from the sample barcode. Reads lacking a known sample barcode or the primer annealing sequence in one end are presumed to derive from an end+internal fragment.

EXAMPLE 7

Consensus Unique Molecular Tags and Elimination of Recombinants

Figure 3:
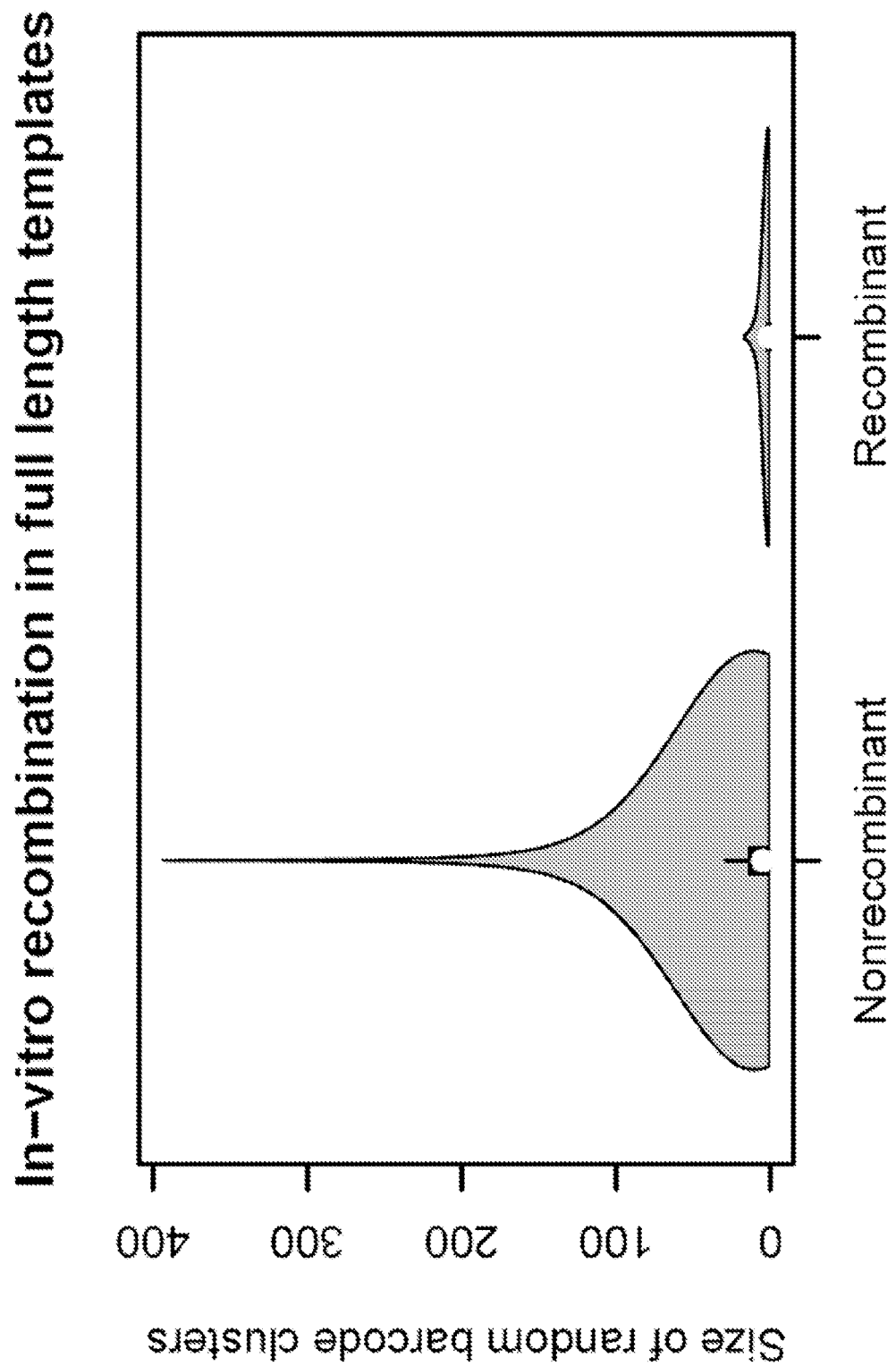
FIG. 3. Abundance of barcode clusters identified as putatively recombinant (left column), along with abundances of the progenitor molecules producing recombinant forms (right). Parental templates are on average 28-35× more abundant than the putatively recombinant forms.

Due to sequencing error, the reads derived from the same template molecule may have slightly different 10 nt unique molecular tag sequences. To estimate the original 10 nt random barcode sequences of tagged template molecules we apply the uclust (Edgar, R. C. (2010) Search and clustering orders of magnitude faster than BLAST, Bioinformatics 26(19), 2460-2461; Edgar, R. C. (2013) UPARSE: Highly accurate OTU sequences from microbial amplicon reads, Nature methods) algorithm to identify clusters of matching random barcode sequences at >89% identity (e.g. 1 out of 10 bases are allowed to mismatch), and to report the consensus sequences of these clusters. We first identify clusters of random barcodes in the end+end fragments. We then identify the highest abundance cluster with each 10 nt random barcode and discard any cluster containing a 10 nt random barcode that was found in a different, more abundant cluster. This step aims to identify and discard combinations of random barcodes that arose due to in-vitro recombination. Recombinant forms are likely to be at lower abundance than the parental templates (FIG. 3). We note that when sequencing arbitrary 2 Kbp fragments, such in vitro recombination is not expected to occur very frequently due to the diversity of the template molecule pool. Recombination detection is most important for application to amplicon sequencing protocols such as for the 16S.

The end+end fragments may not capture all random barcodes present in a sample. The remaining random barcodes might still be used to reconstruct 16S sequences even though they can not be assigned to a sample without end+end fragment information. Therefore, we apply uclust again to identify clusters of random barcodes on each end separately, and add any new consensus sequences that were not previously found in an end+end fragment.

Finally, random barcodes from entire set of reads are matched against the collection of consensus sequences and the reads are grouped into clusters for later assembly.

EXAMPLE 8

Assembly of Read Clusters

Read clusters contain reads that, with high probability, originate from the same template molecule. We apply a de novo assembly algorithm on the read cluster to reconstruct as much of the original template molecule as possible. The reads are assembled using the A5-miseq pipeline (Tritt et al (2012) An integrated pipeline for de Novo assembly of Microbial Genomes, PLoS One). A5-miseq is a revision of the original A5 pipeline, extending it to support assembly of reads up to 500 nt long and to trim out adapter sequence from reads instead of discarding reads containing adapter sequence.

This method will be referred to as "long sequencing" and data produced with this method as "long" data, from here-on in.

EXAMPLE 9

Analysis of 16S Reads 12 foot samples were sequenced with the full length protocol, 6 of which were sequence twice with the method. All 12 samples were also sequenced using the Caparoso et al 2012 method.

Both V4 and long reads were analysed using the software package QIIME (Caparoso et al (2010), QIME allows analysis of high-throughput community sequence data, Nature Methods 7: 335-335). V4 reads were quality filtered by removing reads less than 248 or more than 253 bp. For comparison, the corresponding V4 region was extracted from the long dataset, and only those assembled sequences that included the V4 region were included in the downstream analysis. These extracted sequences will be referred to as "long-V4" from here on in. All sequences were clustered into OTUs using the closed reference picking method, which assigns sequences to pre-clustered OTUs from a chimera free database (Greengenes). Taxonomy was assessed based on membership to the database of pre-clustered OUTs.

Short Sequencing

A total of 296864 paired end V4 sequences were generated from 12 foot samples and a positive (*Escherichia coli* DNA only) and negative (swab only) control. Of these sequences, 11240 could not be assigned to a sample because of incorrect forward and reverse barcode combinations, indicating a recombination rate of at least 3.8%. 240938 sequences mapped to the 12 foot samples, which was reduced to 240426 after quality filtering (see Table 1 below for number of sequences assigned to each sample). OTUs clustered with the closed reference method in QIIME resulted in 1177 OTUs at 97% similarity containing 2 or more sequences. The taxonomic distribution of these OTUs was similar to what has been reported previously for skin communities, dominated by Firmicutes (79.6%±25.7), Actinobacteria (9.3%±12.9), and Proteobacteria (9.9%±22.2).

TABLE 1

Number of sequences analysed per sample for the different sequencing methods

| | Number of sequences after quality filtering | | |
|---|---|---|---|
| Sample | V4 | Long | Long_V4 |
| F1.B1 | 29853 | 69 | 69 |
| F1.H | 10241 | 37 | 37 |
| F2.B2 | 6501 | 30 | 30 |
| F2.H | 5560 | 80 | 80 |
| F3.B2 | 5258 | 4 | 4 |
| F3.H | 38108 | 85 | 85 |
| F4.LB | 5647 | 32 | 32 |

TABLE 1-continued

Number of sequences analysed per sample for the different sequencing methods

| Sample | Number of sequences after quality filtering | | |
|---|---|---|---|
| | V4 | Long | Long_V4 |
| F4.LH | 3266 | 24 | 24 |
| F5.LB | 13931 | 505 | 505 |
| F5.LH | 66398 | 836 | 836 |
| F6.LB | 33714 | 431 | 431 |
| F6.LH | 21949 | 218 | 218 |
| Total | 240426 | 2351 | 2351 |

Figure 4:
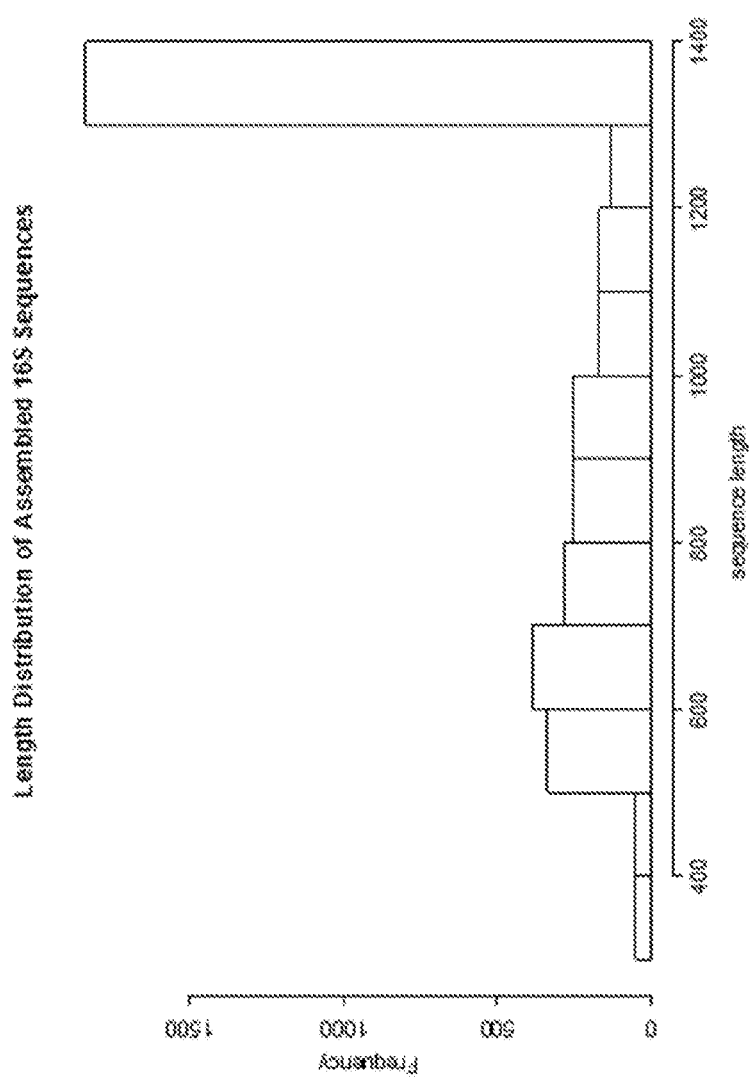
FIG. 4. Graph illustrating the length distribution of the assembled 16S sequences.

Long Sequences 3914 16S sequences were assembled, with 2030 of these being longer than 1000 bp (FIG. 4). 2957 sequences were assigned to foot samples, while 957 sequences could not be assigned to a sample because of incorrect molecular tag combinations. Only reads which contained a V4 region corresponding to that sequenced with the short sequencing method were used for downstream analysis, and these sequences were quality filtered in QIIME by removing sequences shorter than 700 bp and longer than 1500 bp. This resulted in 2351 sequences used for analysis (see Table 1 for details of how many sequences were assigned to each sample).

Figure 5:
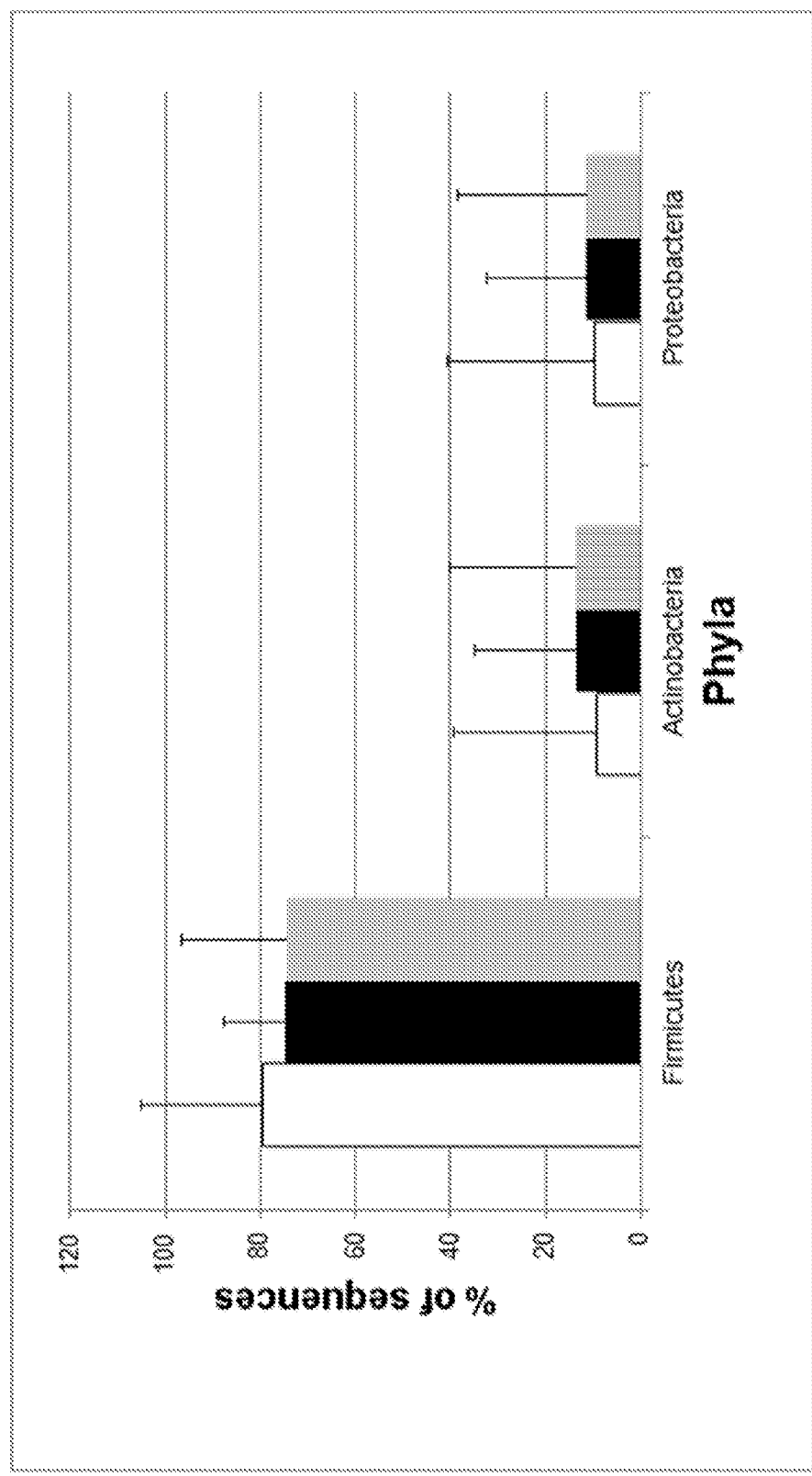
FIG. 5. Graph comparing phyla level taxonomic assignments of OTUs using long and short sequences. The clear bar represents the average value across all 12 samples for the short sequencing method. The black bar represents the average value across all 12 samples for the "long" method. The grey bar represents the average value across all 12 samples from the assembled V4 region from the "long" sequencing method.

Long reads (2351 used for analysis) clustered into 72 OTUs, while the V4-long sequences (corresponding to the same region as the V4 dataset) clustered into 48 OTUs. These OTUs showed the same broad taxonomic distribution as the V4 sequence data (FIG. 5). Although there was a small increase in the representation of Actinobacteria (13.6%±21.6) and Proteobacteria (11.4±26.7), these differences were not significant (two tailed t-test, p>0.05).

Figure 6:
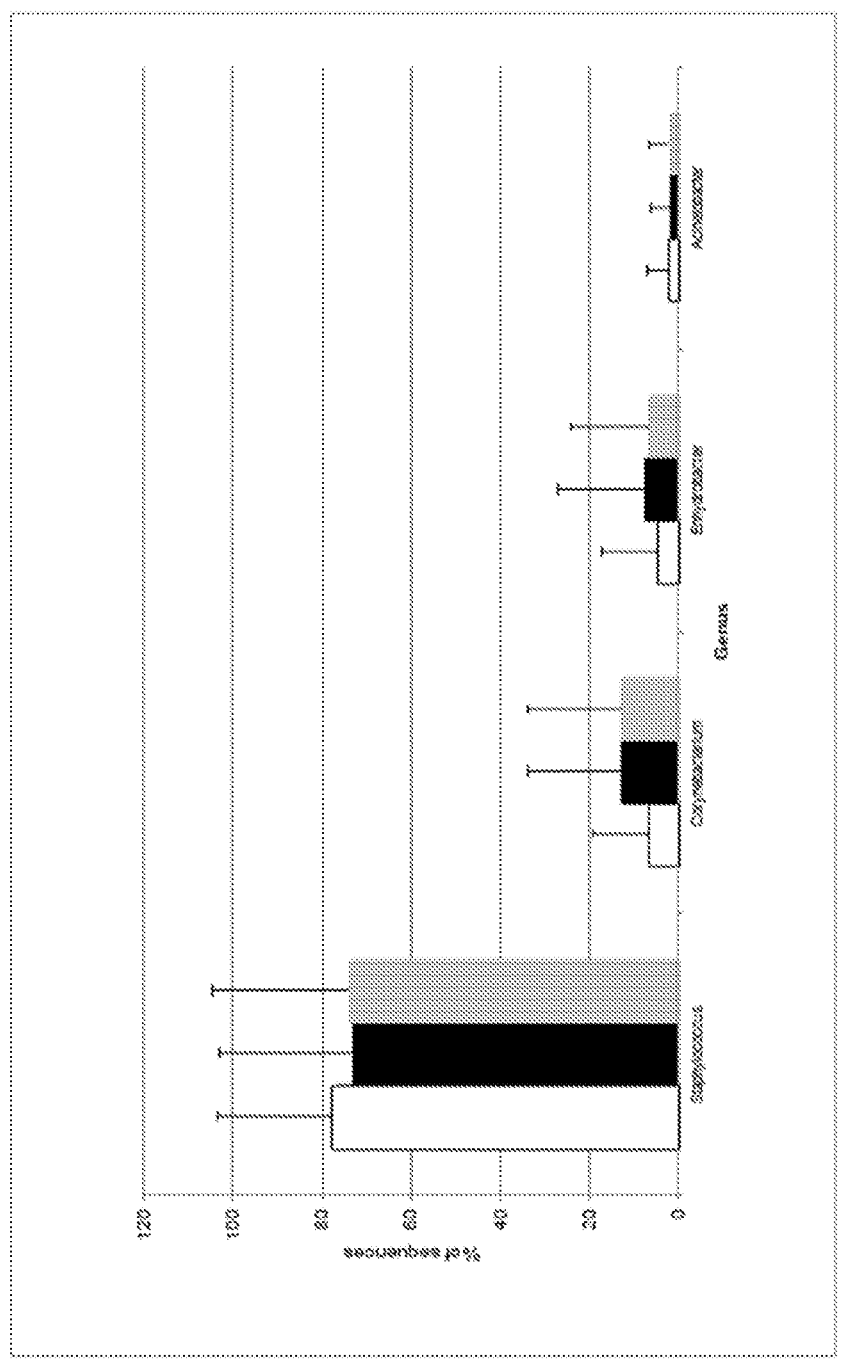
FIG. 6. Graph comparing genus level taxonomic assignments of OTUs using long and short sequences. The clear bar represents the average value across all 12 samples for the short sequencing method. The black bar represents the average value across all 12 samples for the "long" method. The grey bar represents the average value across all 12 samples from the assembled V4 region from the long sequencing method.

Similar taxonomic assignments were also observed at the level of genus (FIG. 6), with communities dominated by Staphylococcus, followed by *Corynebacterium, Enhydrobacter* and *Acinetobacter genera*. The *Corynebacterium* genus had an increased representation in the long data set as compared to the short sequencing method, which likely accounts for the observed difference in representation for the *Actinobacteria phyla*, but as above, this difference was not significant (two tailed t-test, p>0.05). Comparison of individual samples between the short sequencing and long methods showed that Corynebacteria were not consistently over-represented in the assembled dataset, and the average was strongly influenced by one sample where Corynebacterium represented only 0.03% sequences in the V4 sample, but 46.67% of sequences in the assembled long sequencing data (sample F2 B2).

Recombination Rates

Comparison at the OTU Level

Assembled 16S sequences (lengths varying from 756 to 1375) were clustered in OTUs using the closed reference method in QIIME, and shared on average only 30.1%(±6.8) of OTUs with matched sample V4 data which was clustered in the same way. This may be due to comparing datasets of different lengths, and the way in which OTUs are clustered in QIIME. Sequences are assigned to OTUs by the best match against a database of sequences, which have been pre-clustered into OTUs at 97% similarity. Presumably, full length sequences from the database were used to cluster OTUs, and clusters that are 97% similar across the full 16S gene, may not be 97% similar in the V4 region only, since different regions of the 16S gene evolve at different rates (Schloss P D (2010) The Effects of Alignment Quality, Distance Calculation Method, Sequence Filtering, and Region on the Analysis of 16S rRNA Gene-Based Studies. Plos Computational Biology 6). We therefore analysed OTUs clustered from the V4 region only of the long sequences (long-V4 sequences). In this case 92.2%(±12.1) of OTUs were shared with the matched Caporaso sample OTUs (Table 3). Although a lower coverage of sequencing was obtained in the long data set, and subsequently much fewer OTUs overall, this shows that the data that was obtained is broadly concurrent with that obtained using short V4 sequences. Interestingly, the long sequences clustered into ~50% more OTUs than the long-V4 sequences, demonstrating the more sensitive classification achievable with more sequence information per 16S molecule.

This data indicates that this newly developed method gives broadly concurrent community profiles with respect to taxonomy and OTU clustering, and allows for more sensitive taxonomic assignment.

EXAMPLE 10

Sequencing Long Fragments from *E. coli* K12 MG1655

Figure 7:
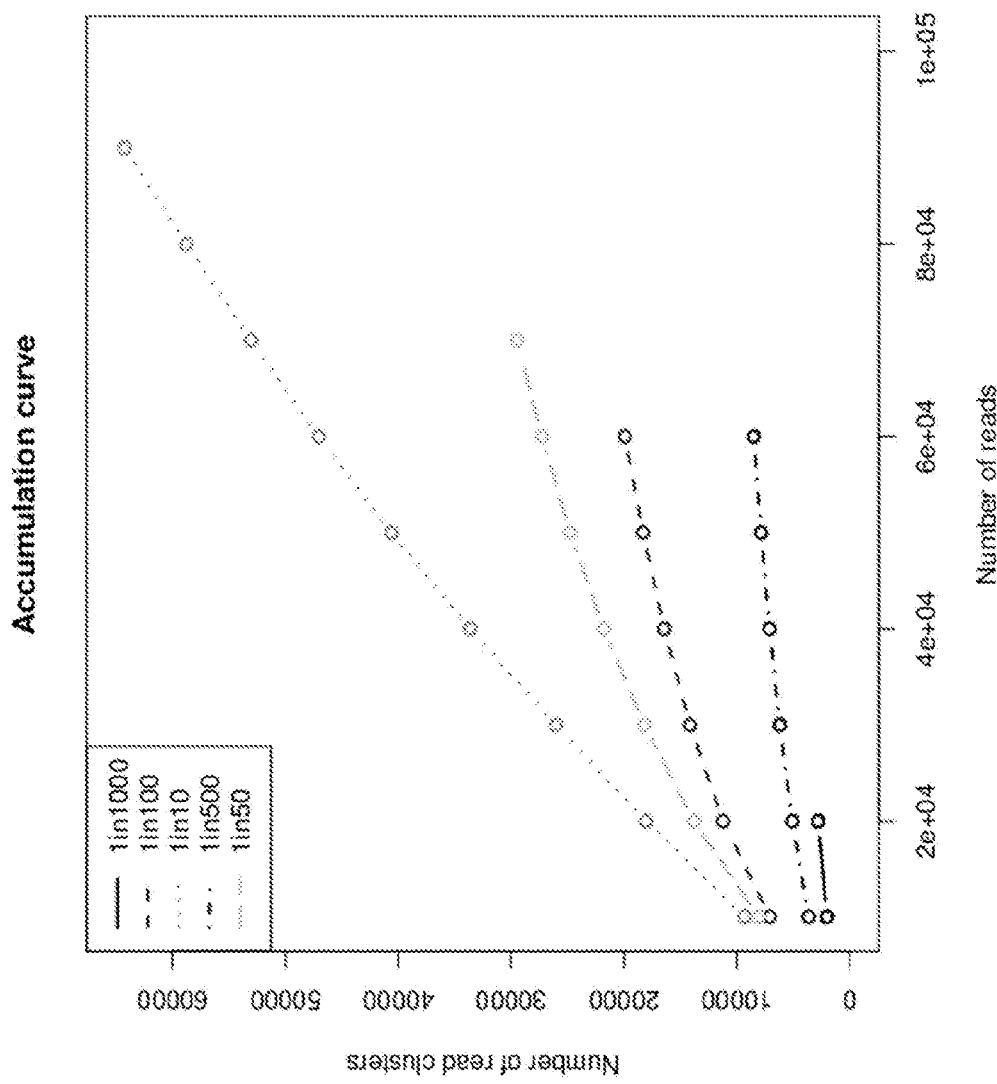
FIG. 7. Accumulation curves showing the number of random barcodes observed versus the number of template molecules sequenced. The 50× and 100× dilutions were predicted to have an appropriate level of redundancy in templates to permit reconstruction of the full length template molecule by fill-in sequencing on an Illumina MiSeq. The top line represents a 1 in 10 dilution, the second line from the top represents a 1 in 50 dilution. The third line from the top represents a 1 in 100 dilution. The fourth line from the top represents a 1 in 500 dilution and the bottom line represents a 1 in 1000 dilution.

Genomic DNA from *E. coli* K12 MG1655 was tagmented and fragments 1.5-3 kbp were size selected using agarose gel electrophoresis. Molecular tagging was applied to these fragments via 2 cycles PCR with random barcodes. Initial sequencing of the pool revealed an excess of diversity among template molecules, such that reconstruction of full length templates would be infeasible. A dilution series was used to determine the appropriate degree to which the population of template molecules should be bottlenecked for successful sequencing & reconstruction of full length templates (FIG. 7). Both 50× and 100× dilutions were sequenced with fill-in reads.

The invention claimed is:

1. A method for generating sequences of at least one target template nucleic acid molecule comprising:
   a) providing at least one sample of nucleic acid molecules comprising at least two target template nucleic acid molecules;
   b) tagging each of the at least two target template nucleic acid molecules with a unique first molecular tag and a unique second molecular tag, wherein tagging each of the at least two target template nucleic acid molecules comprises introducing a unique first molecular tag and a stub sequence into one end of each of the at least two target template nucleic acid molecules and a unique second molecular tag and a stub sequence into the other end of each of the at least two target template nucleic acid molecules, thereby to provide at least two tagged template nucleic acid molecules wherein each of the at least two tagged template nucleic acid molecules is tagged with a unique first molecular tag and a unique second molecular tag;
   c) amplifying the at least two tagged template nucleic acid molecules using primers which comprise a region which is capable of hybridising to the stub sequence at each end of the tagged template nucleic acid molecules to provide multiple copies of the at least two tagged template nucleic acid molecules, wherein each of the copies of the at least two tagged template nucleic acid molecules comprises a first molecular tag and a second molecular tag;
   d) sequencing regions of the multiple copies of the at least two tagged template nucleic acid molecules comprising the first molecular tag and the second molecular tag, wherein sequencing regions of the multiple copies of the at least two tagged template nucleic acid molecules comprises sequencing the first molecular tag and sequencing the second molecular tag of each of the multiple copies of the at least two tagged template nucleic acid molecules; and
   e) reconstructing a consensus sequence for at least one of the at least two target template nucleic acid molecules;
   wherein step e) comprises
   (i) identifying clusters of sequences of the multiple copies of the at least two tagged template nucleic acid molecules which are likely to correspond to the same target template nucleic acid molecule by assigning sequences comprising first molecular tag sequences which are homologous to one another and second molecular tag sequences which are homologous to one another to the same cluster;
   (ii) selecting at least one cluster of sequences wherein the sequences within the selected cluster comprise a first molecular tag and a second molecular tag which are more commonly associated with one another than with a different first molecular tag or second molecular tag;
   (iii) reconstructing a consensus sequence of a target template nucleic acid molecule by aligning sequences in the cluster selected in step (ii), and defining a consensus sequence from the aligned sequences; and optionally (iv) performing steps (ii) to (iii) in respect of a second and/or further template nucleic acid molecule.

2. A computer-implemented method for determining sequences of at least one individual target template nucleic acid molecule comprising the following steps:
(a) obtaining data comprising sequences of regions of multiple copies of at least two tagged template nucleic acid molecules wherein each of the at least two tagged template nucleic acid molecules is tagged with a unique first molecular tag and a unique second molecular tag and comprises the unique first molecular tag at one end and the unique second molecular tag at the other end, wherein each tag and wherein the regions comprise the first molecular tag and the second molecular tag, wherein the data comprises the sequence of the first molecular tag and the sequence of the second molecular tag of each of the multiple copies of the at least two tagged template nucleic acid molecules;
(b) analysing the data comprising the sequences of the regions of the multiple copies of the at least two tagged template nucleic acid molecules comprising the sequence of the first molecular tag and the sequence of the second molecular tag to identify clusters of sequences which are likely to correspond to the same template nucleic acid molecule by assigning sequences comprising first molecular tags which are homologous to one another and second molecular tags which are homologous to one another to the same cluster;
(c) selecting at least one cluster of sequences wherein the sequences within the selected cluster comprise a first molecular tag and a second molecular tag which are more commonly associated with one another than with a different first molecular tag or second molecular tag;
(d) reconstructing a consensus sequence of a first target template nucleic acid molecule by aligning at least a subset of the sequences in the cluster selected in step (c), and defining a consensus sequence from the aligned sequences; and optionally
(e) performing steps (c) to (d) in respect of a second and/or further target template nucleic acid molecule.

3. The method of claim 2, wherein the first and second molecular tag are greater than 5 base pairs in size.

4. The method of claim 2, wherein the first and second molecular tag are greater than 7 base pairs in size.

5. The method of claim 2, wherein the at least two target template nucleic acid molecules are greater than 1 kb in size.

6. The method of claim 2, wherein reconstructing a consensus sequence of a first target template nucleic acid molecule by aligning at least a subset of the sequences molecules in the cluster selected in step (c) is conducted without regard to clusters of sequences that comprise a first molecular tag associated with a second molecular tag that is at least 10 times less commonly associated with the first molecular tag than the second molecular tag that it is most commonly associated with.

7. The method of claim 1, wherein step (e)(iv) consists of identifying groups of clusters of sequences of the at least two tagged template nucleic acid molecules wherein the sequences within the clusters of each group have 5' molecular tags which are homologous to one another and/or identifying groups of clusters of sequences of the at least two tagged template nucleic acid molecules wherein the sequences within the clusters of each group have 3' molecular tags which are homologous to one another; and selecting a cluster from a group of clusters of sequences wherein the cluster that is selected contains the highest number of sequences.

8. The method of claim 1, wherein:
(A) the first molecular tags of the sequences of the same cluster have at least 90% sequence identity to one another; and/or
(B) the second molecular tags of the sequences of the same cluster have at least 90% sequence identity to one another.

9. The method of claim 1, wherein:
(A) the regions comprise greater than 25 base pairs comprising the first molecular tag or the second molecular tag; and/or
(B) the regions comprise the entire length of the at least two tagged template nucleic acid molecules; and/or
(C) the first molecular tag and the second molecular tag are introduced into the at least two template nucleic acid molecules using a method selected from the group consisting of PCR, tagmentation, and physical shearing or restriction digestion of the at least one template nucleic acid molecule followed by ligation of nucleic acids comprising the 5' molecular tag or the 3' molecular tag.

10. The method of claim 9, wherein in (C) the first molecular tag and the second molecular tag are introduced into the at least two template nucleic acid molecules by PCR using primers comprising a portion comprising the first molecular tag or the second molecular tag and a portion having a sequence that is capable of hybridising to the at least two template nucleic acid molecules.

11. The method of claim 1, wherein:
(A) the at least two template nucleic acid molecules encode microbial ribosomal 16S sequences; and/or
(B) at least one of the at least two template nucleic acid molecules is less than 10 Kbp in size.

12. The method of claim 1, wherein the first and second molecular tag are greater than 5 base pairs in size.

13. The method of claim 1, wherein the first and second molecular tag are greater than 7 base pairs in size.

14. The method of claim 1, wherein the at least two target template nucleic acid molecules are greater than 1 kb in size.

15. The method of claim 1, wherein:
(A) the first molecular tags of the sequences of the same cluster have at least 90% sequence identity to one another; and/or
(B) the second molecular tags of the sequences of the same cluster have at least 90% sequence identity to one another.

16. The method of claim 1, wherein:
(A) the first molecular tags of the sequences of the same cluster have at least 90% sequence identity to one another; and/or
(B) the second molecular tags of the sequences of the same cluster have at least 90% sequence identity to one another.

17. The method of claim 1, wherein reconstructing a consensus sequence of a first target template nucleic acid molecule by aligning sequences of the at least two template nucleic acid molecules in the cluster selected in step (ii) is conducted without regard to clusters of sequences that comprise a first molecular tag associated with a second molecular tag that is at least 10 times less commonly associated with the first molecular tag than the second molecular tag that it is most commonly associated with.

* * * * *

SEQUENCE LISTING

```
<160> NUMBER OF SEQ ID NOS: 82

<210> SEQ ID NO 1
<211> LENGTH: 73
<212> TYPE: DNA
<213> ORGANISM: Artificial Sequence
<220> FEATURE:
<223> OTHER INFORMATION: Long_forward_1
<220> FEATURE:
<221> NAME/KEY: misc_feature
<222> LOCATION: (34)..(43)
<223> OTHER INFORMATION: n is a, c, g, or t

<400> SEQUENCE: 1
```
acactctttc cctacacgac gctcttccga tctnnnnnnn nnngttggcc gcgagagttt    60
gatcmtggct cag    73

<210> SEQ ID NO 2
<211> LENGTH: 74
<212> TYPE: DNA
<213> ORGANISM: Artificial Sequence
<220> FEATURE:
<223> OTHER INFORMATION: Long_forward_2
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 2
acactctttc cctacacgac gctcttccga tctnnnnnnn nnntattaac tncgagagtt    60
tgatcmtggc tcag    74

<210> SEQ ID NO 3
<211> LENGTH: 75
<212> TYPE: DNA
<213> ORGANISM: Artificial Sequence
<220> FEATURE:
<223> OTHER INFORMATION: Long_forward_3
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 3
acactctttc cctacacgac gctcttccga tctnnnnnnn nnnctaatgg cnncgagagt    60
ttgatcmtgg ctcag    75

<210> SEQ ID NO 4
<211> LENGTH: 76
<212> TYPE: DNA
<213> ORGANISM: Artificial Sequence
<220> FEATURE:
<223> OTHER INFORMATION: Long_forward_4
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 4
acactctttc cctacacgac gctcttccga tctnnnnnnn nnnaaccagt cnnncgagag    60
tttgatcmtg gctcag    76

<210> SEQ ID NO 5
<211> LENGTH: 73
<212> TYPE: DNA
<213> ORGANISM: Artificial Sequence
<220> FEATURE:
<223> OTHER INFORMATION: Long_forward_5
<220> FEATURE:

```
<221> NAME/KEY: misc_feature
<222> LOCATION: (34)..(43)
<223> OTHER INFORMATION: n is a, c, g, or t

<400> SEQUENCE: 5
acactctttc cctacacgac gctcttccga tctnnnnnnn nnngaacgga gcgagagttt    60
gatcmtggct cag                                                      73

<210> SEQ ID NO 6
<211> LENGTH: 74
<212> TYPE: DNA
<213> ORGANISM: Artificial Sequence
<220> FEATURE:
<223> OTHER INFORMATION: Long_forward_6
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 6
acactctttc cctacacgac gctcttccga tctnnnnnnn nnnactgaag tncgagagtt    60
tgatcmtggc tcag                                                     74

<210> SEQ ID NO 7
<211> LENGTH: 75
<212> TYPE: DNA
<213> ORGANISM: Artificial Sequence
<220> FEATURE:
<223> OTHER INFORMATION: Long_forward_7
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 7
acactctttc cctacacgac gctcttccga tctnnnnnnn nnnttggcta tnncgagagt    60
ttgatcmtgg ctcag                                                    75

<210> SEQ ID NO 8
<211> LENGTH: 76
<212> TYPE: DNA
<213> ORGANISM: Artificial Sequence
<220> FEATURE:
<223> OTHER INFORMATION: Long_forward_8
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 8
acactctttc cctacacgac gctcttccga tctnnnnnnn nnntggcgat tnnncgagag    60
tttgatcmtg gctcag                                                   76

<210> SEQ ID NO 9
<211> LENGTH: 73
```

```
<212> TYPE: DNA
<213> ORGANISM: Artificial Sequence
<220> FEATURE:
<223> OTHER INFORMATION: Long_forward_9
<220> FEATURE:
<221> NAME/KEY: misc_feature
<222> LOCATION: (34)..(43)
<223> OTHER INFORMATION: n is a, c, g, or t

<400> SEQUENCE: 9
acactctttc cctacacgac gctcttccga tctnnnnnnn nnncctctga tcgagagttt      60
gatcmtggct cag                                                        73

<210> SEQ ID NO 10
<211> LENGTH: 74
<212> TYPE: DNA
<213> ORGANISM: Artificial Sequence
<220> FEATURE:
<223> OTHER INFORMATION: Long_forward_10
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 10
acactctttc cctacacgac gctcttccga tctnnnnnnn nnnctcatgc gncgagagtt      60
tgatcmtggc tcag                                                       74

<210> SEQ ID NO 11
<211> LENGTH: 75
<212> TYPE: DNA
<213> ORGANISM: Artificial Sequence
<220> FEATURE:
<223> OTHER INFORMATION: Long_forward_11
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 11
acactctttc cctacacgac gctcttccga tctnnnnnnn nnnttcagcg anncgagagt      60
ttgatcmtgg ctcag                                                      75

<210> SEQ ID NO 12
<211> LENGTH: 76
<212> TYPE: DNA
<213> ORGANISM: Artificial Sequence
<220> FEATURE:
<223> OTHER INFORMATION: Long_forward_12
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 12
acactctttc cctacacgac gctcttccga tctnnnnnnn nnnggatgcc annncgagag      60
```
tttgatcmtg gctcag                                                          76

<210> SEQ ID NO 13
<211> LENGTH: 73
<212> TYPE: DNA
<213> ORGANISM: Artificial Sequence
<220> FEATURE:
<223> OTHER INFORMATION: Long_forward_13
<220> FEATURE:
<221> NAME/KEY: misc_feature
<222> LOCATION: (34)..(43)
<223> OTHER INFORMATION: n is a, c, g, or t

<400> SEQUENCE: 13
acactctttc cctacacgac gctcttccga tctnnnnnnn nnncggtcga gcgagagttt         60
gatcmtggct cag                                                            73

<210> SEQ ID NO 14
<211> LENGTH: 74
<212> TYPE: DNA
<213> ORGANISM: Artificial Sequence
<220> FEATURE:
<223> OTHER INFORMATION: Long_forward_14
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 14
acactctttc cctacacgac gctcttccga tctnnnnnnn nnnaagacta cncgagagtt         60
tgatcmtggc tcag                                                           74

<210> SEQ ID NO 15
<211> LENGTH: 75
<212> TYPE: DNA
<213> ORGANISM: Artificial Sequence
<220> FEATURE:
<223> OTHER INFORMATION: Long_forward_15
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 15
acactctttc cctacacgac gctcttccga tctnnnnnnn nnnaacgcta anncgagagt         60
ttgatcmtgg ctcag                                                          75

<210> SEQ ID NO 16
<211> LENGTH: 76
<212> TYPE: DNA
<213> ORGANISM: Artificial Sequence
<220> FEATURE:
<223> OTHER INFORMATION: Long_forward_16
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 16
acactctttc cctacacgac gctcttccga tctnnnnnnn nnngcctacg cnnncgagag    60
tttgatcmtg gctcag                                                   76

<210> SEQ ID NO 17
<211> LENGTH: 73
<212> TYPE: DNA
<213> ORGANISM: Artificial Sequence
<220> FEATURE:
<223> OTHER INFORMATION: Long_forward_17
<220> FEATURE:
<221> NAME/KEY: misc_feature
<222> LOCATION: (34)..(43)
<223> OTHER INFORMATION: n is a, c, g, or t

<400> SEQUENCE: 17
acactctttc cctacacgac gctcttccga tctnnnnnnn nnntgactgc tcgagagttt    60
gatcmtggct cag                                                      73

<210> SEQ ID NO 18
<211> LENGTH: 75
<212> TYPE: DNA
<213> ORGANISM: Artificial Sequence
<220> FEATURE:
<223> OTHER INFORMATION: Long_forward_19
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 18
acactctttc cctacacgac gctcttccga tctnnnnnnn nnncaacctt anncgagagt    60
ttgatcmtgg ctcag                                                    75

<210> SEQ ID NO 19
<211> LENGTH: 76
<212> TYPE: DNA
<213> ORGANISM: Artificial Sequence
<220> FEATURE:
<223> OTHER INFORMATION: Long_forward_20
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 19
acactctttc cctacacgac gctcttccga tctnnnnnnn nnnggaggct gnnncgagag    60
tttgatcmtg gctcag                                                   76

<210> SEQ ID NO 20
<211> LENGTH: 73
<212> TYPE: DNA
<213> ORGANISM: Artificial Sequence
<220> FEATURE:
<223> OTHER INFORMATION: Long_forward_21
<220> FEATURE:
<221> NAME/KEY: misc_feature
<222> LOCATION: (34)..(43)

<223> OTHER INFORMATION: n is a, c, g, or t

<400> SEQUENCE: 20
acactctttc cctacacgac gctcttccga tctnnnnnnn nnnaatcgat acgagagttt    60
gatcmtggct cag                                                      73

<210> SEQ ID NO 21
<211> LENGTH: 74
<212> TYPE: DNA
<213> ORGANISM: Artificial Sequence
<220> FEATURE:
<223> OTHER INFORMATION: Long_forward_22
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 21
acactctttc cctacacgac gctcttccga tctnnnnnnn nnnaccaatt gncgagagtt    60
tgatcmtggc tcag                                                     74

<210> SEQ ID NO 22
<211> LENGTH: 75
<212> TYPE: DNA
<213> ORGANISM: Artificial Sequence
<220> FEATURE:
<223> OTHER INFORMATION: Long_forward_23
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 22
acactctttc cctacacgac gctcttccga tctnnnnnnn nnncctaata anncgagagt    60
ttgatcmtgg ctcag                                                    75

<210> SEQ ID NO 23
<211> LENGTH: 76
<212> TYPE: DNA
<213> ORGANISM: Artificial Sequence
<220> FEATURE:
<223> OTHER INFORMATION: Long_forward_24
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 23
acactctttc cctacacgac gctcttccga tctnnnnnnn nnnggattag gnnncgagag    60
tttgatcmtg gctcag                                                   76

<210> SEQ ID NO 24
<211> LENGTH: 73
<212> TYPE: DNA
<213> ORGANISM: Artificial Sequence
<220> FEATURE:
<223> OTHER INFORMATION: Long_forward_25
<220> FEATURE:
<221> NAME/KEY: misc_feature
<222> LOCATION: (34)..(43)
<223> OTHER INFORMATION: n is a, c, g, or t

<400> SEQUENCE: 24
acactctttc cctacacgac gctcttccga tctnnnnnnn nnngcgttac ccgagagttt      60
gatcmtggct cag                                                        73

<210> SEQ ID NO 25
<211> LENGTH: 70
<212> TYPE: DNA
<213> ORGANISM: Artificial Sequence
<220> FEATURE:
<223> OTHER INFORMATION: Long_reverse_1
<220> FEATURE:
<221> NAME/KEY: misc_feature
<222> LOCATION: (34)..(43)
<223> OTHER INFORMATION: n is a, c, g, or t

<400> SEQUENCE: 25
ctcggcattc ctgctgaacc gctcttccga tctnnnnnnn nnngttggcc gtagacgggc      60 ggtgtgtrca                                                            70

<210> SEQ ID NO 26
<211> LENGTH: 73
<212> TYPE: DNA
<213> ORGANISM: Artificial Sequence
<220> FEATURE:
<223> OTHER INFORMATION: Long_reverse_2
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 26
ctcggcattc ctgctgaacc gctcttccga tctnnnnnnn nnntattaac tnnntagacg      60
ggcggtgtgt rca                                                        73

<210> SEQ ID NO 27
<211> LENGTH: 70
<212> TYPE: DNA
<213> ORGANISM: Artificial Sequence
<220> FEATURE:
<223> OTHER INFORMATION: Long_reverse_3
<220> FEATURE:
<221> NAME/KEY: misc_feature
<222> LOCATION: (34)..(43)
<223> OTHER INFORMATION: n is a, c, g, or t

<400> SEQUENCE: 27
ctcggcattc ctgctgaacc gctcttccga tctnnnnnnn nnnctaatgg ctagacgggc      60 ggtgtgtrca                                                            70

<210> SEQ ID NO 28
<211> LENGTH: 73
<212> TYPE: DNA
<213> ORGANISM: Artificial Sequence
<220> FEATURE:
<223> OTHER INFORMATION: Long_reverse_4
<220> FEATURE:

```
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 28
ctcggcattc ctgctgaacc gctcttccga tctnnnnnnn nnnaaccagt cnnntagacg    60
ggcggtgtgt rca                                                      73

<210> SEQ ID NO 29
<211> LENGTH: 70
<212> TYPE: DNA
<213> ORGANISM: Artificial Sequence
<220> FEATURE:
<223> OTHER INFORMATION: Long_reverse_5
<220> FEATURE:
<221> NAME/KEY: misc_feature
<222> LOCATION: (34)..(43)
<223> OTHER INFORMATION: n is a, c, g, or t

<400> SEQUENCE: 29
ctcggcattc ctgctgaacc gctcttccga tctnnnnnnn nnngaacgga gtagacgggc    60 ggtgtgtrca                                                          70

<210> SEQ ID NO 30
<211> LENGTH: 72
<212> TYPE: DNA
<213> ORGANISM: Artificial Sequence
<220> FEATURE:
<223> OTHER INFORMATION: Long_reverse_6
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 30
ctcggcattc ctgctgaacc gctcttccga tctnnnnnnn nnnactgaag tnntagacgg    60
gcggtgtgtr ca                                                       72

<210> SEQ ID NO 31
<211> LENGTH: 73
<212> TYPE: DNA
<213> ORGANISM: Artificial Sequence
<220> FEATURE:
<223> OTHER INFORMATION: Long_reverse_7
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 31
ctcggcattc ctgctgaacc gctcttccga tctnnnnnnn nnnttggcta tnnntagacg    60
ggcggtgtgt rca                                                      73

<210> SEQ ID NO 32
<211> LENGTH: 70
```

```
<212> TYPE: DNA
<213> ORGANISM: Artificial Sequence
<220> FEATURE:
<223> OTHER INFORMATION: Long_reverse_8
<220> FEATURE:
<221> NAME/KEY: misc_feature
<222> LOCATION: (34)..(43)
<223> OTHER INFORMATION: n is a, c, g, or t

<400> SEQUENCE: 32
ctcggcattc ctgctgaacc gctcttccga tctnnnnnnn nnntggcgat ttagacgggc      60 ggtgtgtrca                                                            70

<210> SEQ ID NO 33
<211> LENGTH: 71
<212> TYPE: DNA
<213> ORGANISM: Artificial Sequence
<220> FEATURE:
<223> OTHER INFORMATION: Long_reverse_9
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 33
ctcggcattc ctgctgaacc gctcttccga tctnnnnnnn nnncctctga tntagacggg      60
cggtgtgtrc a                                                          71

<210> SEQ ID NO 34
<211> LENGTH: 72
<212> TYPE: DNA
<213> ORGANISM: Artificial Sequence
<220> FEATURE:
<223> OTHER INFORMATION: Long_reverse_10
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 34
ctcggcattc ctgctgaacc gctcttccga tctnnnnnnn nnnctcatgc gnntagacgg      60
gcggtgtgtr ca                                                         72

<210> SEQ ID NO 35
<211> LENGTH: 71
<212> TYPE: DNA
<213> ORGANISM: Artificial Sequence
<220> FEATURE:
<223> OTHER INFORMATION: Long_reverse_11
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 35
ctcggcattc ctgctgaacc gctcttccga tctnnnnnnn nnnttcagcg antagacggg      60
```
cggtgtgtrc a                                                              71

<210> SEQ ID NO 36
<211> LENGTH: 72
<212> TYPE: DNA
<213> ORGANISM: Artificial Sequence
<220> FEATURE:
<223> OTHER INFORMATION: Long_reverse_12
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 36
ctcggcattc ctgctgaacc gctcttccga tctnnnnnnn nnnggatgcc anntagacgg        60
gcggtgtgtr ca                                                             72

<210> SEQ ID NO 37
<211> LENGTH: 71
<212> TYPE: DNA
<213> ORGANISM: Artificial Sequence
<220> FEATURE:
<223> OTHER INFORMATION: Long_reverse_13
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 37
ctcggcattc ctgctgaacc gctcttccga tctnnnnnnn nnncggtcga gntagacggg        60
cggtgtgtrc a                                                              71

<210> SEQ ID NO 38
<211> LENGTH: 73
<212> TYPE: DNA
<213> ORGANISM: Artificial Sequence
<220> FEATURE:
<223> OTHER INFORMATION: Long_reverse_14
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 38
ctcggcattc ctgctgaacc gctcttccga tctnnnnnnn nnnaagacta cnnntagacg        60
ggcggtgtgt rca                                                            73

<210> SEQ ID NO 39
<211> LENGTH: 70
<212> TYPE: DNA
<213> ORGANISM: Artificial Sequence
<220> FEATURE:
<223> OTHER INFORMATION: Long_reverse_15
<220> FEATURE:
<221> NAME/KEY: misc_feature
<222> LOCATION: (34)..(43)
<223> OTHER INFORMATION: n is a, c, g, or t

<400> SEQUENCE: 39
ctcggcattc ctgctgaacc gctcttccga tctnnnnnnn nnnaacgcta atagacgggc    60 ggtgtgtrca                                                           70

<210> SEQ ID NO 40
<211> LENGTH: 71
<212> TYPE: DNA
<213> ORGANISM: Artificial Sequence
<220> FEATURE:
<223> OTHER INFORMATION: Long_reverse_16
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 40
ctcggcattc ctgctgaacc gctcttccga tctnnnnnnn nnngcctacg cntagacggg    60
cggtgtgtrc a                                                         71

<210> SEQ ID NO 41
<211> LENGTH: 72
<212> TYPE: DNA
<213> ORGANISM: Artificial Sequence
<220> FEATURE:
<223> OTHER INFORMATION: Long_reverse_17
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 41
ctcggcattc ctgctgaacc gctcttccga tctnnnnnnn nnntgactgc tnntagacgg    60
gcggtgtgtr ca                                                        72

<210> SEQ ID NO 42
<211> LENGTH: 71
<212> TYPE: DNA
<213> ORGANISM: Artificial Sequence
<220> FEATURE:
<223> OTHER INFORMATION: Long_reverse_18
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 42
ctcggcattc ctgctgaacc gctcttccga tctnnnnnnn nnnattgccg cntagacggg    60
cggtgtgtrc a                                                         71

<210> SEQ ID NO 43
<211> LENGTH: 72
<212> TYPE: DNA
<213> ORGANISM: Artificial Sequence
<220> FEATURE:

```
<223> OTHER INFORMATION: Long_reverse_19
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 43
ctcggcattc ctgctgaacc gctcttccga tctnnnnnnn nnncaacctt anntagacgg    60
gcggtgtgtr ca                                                        72

<210> SEQ ID NO 44
<211> LENGTH: 71
<212> TYPE: DNA
<213> ORGANISM: Artificial Sequence
<220> FEATURE:
<223> OTHER INFORMATION: Long_reverse_20
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 44
ctcggcattc ctgctgaacc gctcttccga tctnnnnnnn nnnggaggct gntagacggg    60
cggtgtgtrc a                                                         71

<210> SEQ ID NO 45
<211> LENGTH: 72
<212> TYPE: DNA
<213> ORGANISM: Artificial Sequence
<220> FEATURE:
<223> OTHER INFORMATION: Long_reverse_21
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 45
ctcggcattc ctgctgaacc gctcttccga tctnnnnnnn nnnaatcgat anntagacgg    60
gcggtgtgtr ca                                                        72

<210> SEQ ID NO 46
<211> LENGTH: 71
<212> TYPE: DNA
<213> ORGANISM: Artificial Sequence
<220> FEATURE:
<223> OTHER INFORMATION: Long_reverse_22
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 46
ctcggcattc ctgctgaacc gctcttccga tctnnnnnnn nnnaccaatt gntagacggg    60
```
cggtgtgtrc a                                                               71

<210> SEQ ID NO 47
<211> LENGTH: 71
<212> TYPE: DNA
<213> ORGANISM: Artificial Sequence
<220> FEATURE:
<223> OTHER INFORMATION: Long_reverse_23
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 47
ctcggcattc ctgctgaacc gctcttccga tctnnnnnnn nnncctaata antagacggg          60
cggtgtgtrc a                                                               71

<210> SEQ ID NO 48
<211> LENGTH: 72
<212> TYPE: DNA
<213> ORGANISM: Artificial Sequence
<220> FEATURE:
<223> OTHER INFORMATION: Long_reverse_24
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 48
ctcggcattc ctgctgaacc gctcttccga tctnnnnnnn nnnggattag gnntagacgg          60
gcggtgtgtr ca                                                              72

<210> SEQ ID NO 49
<211> LENGTH: 73
<212> TYPE: DNA
<213> ORGANISM: Artificial Sequence
<220> FEATURE:
<223> OTHER INFORMATION: Long_reverse_25
<220> FEATURE:
<221> NAME/KEY: misc_feature
<222> LOCATION: (34)..(43)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 49
ctcggcattc ctgctgaacc gctcttccga tctnnnnnnn nnngcgttac cnnntagacg          60
ggcggtgtgt rca                                                             73

<210> SEQ ID NO 50
<211> LENGTH: 46
<212> TYPE: DNA
<213> ORGANISM: Artificial Sequence
<220> FEATURE:
<223> OTHER INFORMATION: PE_1

<400> SEQUENCE: 50

-continued aatgatacgg cgaccaccga gatctacact ctttccctac acgacg        46

<210> SEQ ID NO 51
<211> LENGTH: 49
<212> TYPE: DNA
<213> ORGANISM: Artificial Sequence
<220> FEATURE:
<223> OTHER INFORMATION: PE_2

<400> SEQUENCE: 51
caagcagaag acggcatacg agatcggtct cggcattcct gctgaaccg       49

<210> SEQ ID NO 52
<211> LENGTH: 68
<212> TYPE: DNA
<213> ORGANISM: Artificial Sequence
<220> FEATURE:
<223> OTHER INFORMATION: Caporaso_forward_1

<400> SEQUENCE: 52
aatgatacgg cgaccaccga gatctacaca accagtctat ggtaattgtg tgccagcmgc    60
cgcggtaa                                                             68

<210> SEQ ID NO 53
<211> LENGTH: 68
<212> TYPE: DNA
<213> ORGANISM: Artificial Sequence
<220> FEATURE:
<223> OTHER INFORMATION: Caporaso_forward_2

<400> SEQUENCE: 53
aatgatacgg cgaccaccga gatctacaca acgctaatat ggtaattgtg tgccagcmgc    60
cgcggtaa                                                             68

<210> SEQ ID NO 54
<211> LENGTH: 68
<212> TYPE: DNA
<213> ORGANISM: Artificial Sequence
<220> FEATURE:
<223> OTHER INFORMATION: Caporaso_forward_3

<400> SEQUENCE: 54
aatgatacgg cgaccaccga gatctacaca agactactat ggtaattgtg tgccagcmgc    60
cgcggtaa                                                             68

<210> SEQ ID NO 55
<211> LENGTH: 68
<212> TYPE: DNA
<213> ORGANISM: Artificial Sequence
<220> FEATURE:
<223> OTHER INFORMATION: Caporaso_forward_4

<400> SEQUENCE: 55
aatgatacgg cgaccaccga gatctacaca atcgatatat ggtaattgtg tgccagcmgc    60
cgcggtaa                                                             68

<210> SEQ ID NO 56
<211> LENGTH: 68
<212> TYPE: DNA
<213> ORGANISM: Artificial Sequence
<220> FEATURE:
<223> OTHER INFORMATION: Caporaso_forward_5

<400> SEQUENCE: 56

```
aatgatacgg cgaccaccga gatctacaca ccaattgtat ggtaattgtg tgccagcmgc    60
cgcggtaa                                                              68

<210> SEQ ID NO 57
<211> LENGTH: 68
<212> TYPE: DNA
<213> ORGANISM: Artificial Sequence
<220> FEATURE:
<223> OTHER INFORMATION: Caporaso_forward_6

<400> SEQUENCE: 57
aatgatacgg cgaccaccga gatctacaca ctgaagttat ggtaattgtg tgccagcmgc    60
cgcggtaa                                                              68

<210> SEQ ID NO 58
<211> LENGTH: 68
<212> TYPE: DNA
<213> ORGANISM: Artificial Sequence
<220> FEATURE:
<223> OTHER INFORMATION: Caporaso_forward_7

<400> SEQUENCE: 58
aatgatacgg cgaccaccga gatctacaca ttgccgctat ggtaattgtg tgccagcmgc    60
cgcggtaa                                                              68

<210> SEQ ID NO 59
<211> LENGTH: 68
<212> TYPE: DNA
<213> ORGANISM: Artificial Sequence
<220> FEATURE:
<223> OTHER INFORMATION: Caporaso_forward_8

<400> SEQUENCE: 59
aatgatacgg cgaccaccga gatctacacc aaccttatat ggtaattgtg tgccagcmgc    60
cgcggtaa                                                              68

<210> SEQ ID NO 60
<211> LENGTH: 68
<212> TYPE: DNA
<213> ORGANISM: Artificial Sequence
<220> FEATURE:
<223> OTHER INFORMATION: Caporaso_forward_9

<400> SEQUENCE: 60
aatgatacgg cgaccaccga gatctacacc ctaataatat ggtaattgtg tgccagcmgc    60
cgcggtaa                                                              68

<210> SEQ ID NO 61
<211> LENGTH: 68
<212> TYPE: DNA
<213> ORGANISM: Artificial Sequence
<220> FEATURE:
<223> OTHER INFORMATION: Caporaso_forward_10

<400> SEQUENCE: 61
aatgatacgg cgaccaccga gatctacacc ctctgattat ggtaattgtg tgccagcmgc    60
cgcggtaa                                                              68

<210> SEQ ID NO 62
<211> LENGTH: 68
<212> TYPE: DNA
```

<213> ORGANISM: Artificial Sequence
<220> FEATURE:
<223> OTHER INFORMATION: Caporaso_forward_14

<400> SEQUENCE: 62
aatgatacgg cgaccaccga gatctacacg aacggagtat ggtaattgtg tgccagcmgc    60
cgcggtaa                                                              68

<210> SEQ ID NO 63
<211> LENGTH: 68
<212> TYPE: DNA
<213> ORGANISM: Artificial Sequence
<220> FEATURE:
<223> OTHER INFORMATION: Caporaso_forward_16

<400> SEQUENCE: 63
aatgatacgg cgaccaccga gatctacacg cgttacctat ggtaattgtg tgccagcmgc    60
cgcggtaa                                                              68

<210> SEQ ID NO 64
<211> LENGTH: 68
<212> TYPE: DNA
<213> ORGANISM: Artificial Sequence
<220> FEATURE:
<223> OTHER INFORMATION: Caporaso_forward_18

<400> SEQUENCE: 64
aatgatacgg cgaccaccga gatctacacg gatgccatat ggtaattgtg tgccagcmgc    60
cgcggtaa                                                              68

<210> SEQ ID NO 65
<211> LENGTH: 68
<212> TYPE: DNA
<213> ORGANISM: Artificial Sequence
<220> FEATURE:
<223> OTHER INFORMATION: Caporaso_forward_20

<400> SEQUENCE: 65
aatgatacgg cgaccaccga gatctacacg ttggccgtat ggtaattgtg tgccagcmgc    60
cgcggtaa                                                              68

<210> SEQ ID NO 66
<211> LENGTH: 68
<212> TYPE: DNA
<213> ORGANISM: Artificial Sequence
<220> FEATURE:
<223> OTHER INFORMATION: Caporaso_forward_22

<400> SEQUENCE: 66
aatgatacgg cgaccaccga gatctacact gactgcttat ggtaattgtg tgccagcmgc    60
cgcggtaa                                                              68

<210> SEQ ID NO 67
<211> LENGTH: 68
<212> TYPE: DNA
<213> ORGANISM: Artificial Sequence
<220> FEATURE:
<223> OTHER INFORMATION: Caporaso_forward_24

<400> SEQUENCE: 67
aatgatacgg cgaccaccga gatctacact tcagcgatat ggtaattgtg tgccagcmgc    60
cgcggtaa                                                              68

<210> SEQ ID NO 68
<211> LENGTH: 64
<212> TYPE: DNA
<213> ORGANISM: Artificial Sequence
<220> FEATURE:
<223> OTHER INFORMATION: Caporaso_reverse_1

<400> SEQUENCE: 68
caagcagaag acggcatacg agataaccag tcagtcagtc agccggacta chvgggtwtc    60
taat                                                                64

<210> SEQ ID NO 69
<211> LENGTH: 64
<212> TYPE: DNA
<213> ORGANISM: Artificial Sequence
<220> FEATURE:
<223> OTHER INFORMATION: Caporaso_reverse_7

<400> SEQUENCE: 69
caagcagaag acggcatacg agatattgcc gcagtcagtc agccggacta chvgggtwtc    60
taat                                                                64

<210> SEQ ID NO 70
<211> LENGTH: 64
<212> TYPE: DNA
<213> ORGANISM: Artificial Sequence
<220> FEATURE:
<223> OTHER INFORMATION: Caporaso_reverse_8

<400> SEQUENCE: 70
caagcagaag acggcatacg agatcaacct aagtcagtc agccggacta chvgggtwtc     60
taat                                                                64

<210> SEQ ID NO 71
<211> LENGTH: 64
<212> TYPE: DNA
<213> ORGANISM: Artificial Sequence
<220> FEATURE:
<223> OTHER INFORMATION: Caporaso_reverse_9

<400> SEQUENCE: 71
caagcagaag acggcatacg agatcctaat aaagtcagtc agccggacta chvgggtwtc    60
taat                                                                64

<210> SEQ ID NO 72
<211> LENGTH: 64
<212> TYPE: DNA
<213> ORGANISM: Artificial Sequence
<220> FEATURE:
<223> OTHER INFORMATION: Caporaso_reverse_15

<400> SEQUENCE: 72
caagcagaag acggcatacg agatgcctac gcagtcagtc agccggacta chvgggtwtc    60
taat                                                                64

<210> SEQ ID NO 73
<211> LENGTH: 64
<212> TYPE: DNA
<213> ORGANISM: Artificial Sequence
<220> FEATURE:
<223> OTHER INFORMATION: Caporaso_reverse_16

```
<400> SEQUENCE: 73
caagcagaag acggcatacg agatgcgtta ccagtcagtc agccggacta chvgggtwtc    60
taat                                                                64

<210> SEQ ID NO 74
<211> LENGTH: 64
<212> TYPE: DNA
<213> ORGANISM: Artificial Sequence
<220> FEATURE:
<223> OTHER INFORMATION: Caporaso_reverse_17

<400> SEQUENCE: 74
caagcagaag acggcatacg agatggaggc tgagtcagtc agccggacta chvgggtwtc    60
taat                                                                64

<210> SEQ ID NO 75
<211> LENGTH: 64
<212> TYPE: DNA
<213> ORGANISM: Artificial Sequence
<220> FEATURE:
<223> OTHER INFORMATION: Caporaso_reverse_23

<400> SEQUENCE: 75
caagcagaag acggcatacg agattggcga ttagtcagtc agccggacta chvgggtwtc    60
taat                                                                64

<210> SEQ ID NO 76
<211> LENGTH: 64
<212> TYPE: DNA
<213> ORGANISM: Artificial Sequence
<220> FEATURE:
<223> OTHER INFORMATION: Caporaso_reverse_24

<400> SEQUENCE: 76
caagcagaag acggcatacg agatttcagc gaagtcagtc agccggacta chvgggtwtc    60
taat                                                                64

<210> SEQ ID NO 77
<211> LENGTH: 64
<212> TYPE: DNA
<213> ORGANISM: Artificial Sequence
<220> FEATURE:
<223> OTHER INFORMATION: Caporaso_reverse_25

<400> SEQUENCE: 77
caagcagaag acggcatacg agatttggct atagtcagtc agccggacta chvgggtwtc    60
taat                                                                64

<210> SEQ ID NO 78
<211> LENGTH: 20
<212> TYPE: DNA
<213> ORGANISM: Artificial Sequence
<220> FEATURE:
<223> OTHER INFORMATION: Illumina_E_1

<400> SEQUENCE: 78
aatgatacgg cgaccaccga                                               20

<210> SEQ ID NO 79
<211> LENGTH: 21
<212> TYPE: DNA
<213> ORGANISM: Artificial Sequence
```

```
<220> FEATURE:
<223> OTHER INFORMATION: Illumina_E_2

<400> SEQUENCE: 79
caagcagaag acggcatacg a                                              21

<210> SEQ ID NO 80
<211> LENGTH: 31
<212> TYPE: DNA
<213> ORGANISM: Artificial Sequence
<220> FEATURE:
<223> OTHER INFORMATION: Caporaso_read_1

<400> SEQUENCE: 80
tatggtaatt gtgtgccagc mgccgcggta a                                   31

<210> SEQ ID NO 81
<211> LENGTH: 32
<212> TYPE: DNA
<213> ORGANISM: Artificial Sequence
<220> FEATURE:
<223> OTHER INFORMATION: Caporaso_read_2

<400> SEQUENCE: 81
agtcagtcag ccggactach vgggtwtcta at                                  32

<210> SEQ ID NO 82
<211> LENGTH: 32
<212> TYPE: DNA
<213> ORGANISM: Artificial Sequence
<220> FEATURE:
<223> OTHER INFORMATION: Caporaso_index_read

<400> SEQUENCE: 82
attagawacc cbdgtagtcc ggctgactga ct                                  32
```